United States Patent
Saffari

(10) Patent No.: US 10,136,506 B2
(45) Date of Patent: Nov. 20, 2018

(54) VARIABLE FREQUENCY LEDS AND TIME-BASED FREQUENCY-VARIABLE DRIVERS FOR LED LIGHTING

(71) Applicant: Dynotron, Inc., Salt Lake City, UT (US)

(72) Inventor: James Saffari, Salt Lake City, UT (US)

(73) Assignee: Dynotron, Inc., Salt Lake City, UT (US)

( * ) Notice: Subject to any disclaimer, the term of this patent is extended or adjusted under 35 U.S.C. 154(b) by 0 days.

(21) Appl. No.: 15/898,918

(22) Filed: Feb. 19, 2018

(65) Prior Publication Data

US 2018/0177034 A1 Jun. 21, 2018

Related U.S. Application Data

(60) Division of application No. 15/377,725, filed on Dec. 13, 2016, now Pat. No. 9,907,148, which is a
(Continued)

(51) Int. Cl.
  *H05B 37/02* (2006.01)
  *H05B 33/08* (2006.01)
  (Continued)

(52) U.S. Cl.
  CPC ......... *H05B 37/0272* (2013.01); *A01G 7/045* (2013.01); *A01G 9/20* (2013.01);
  (Continued)

(58) Field of Classification Search
  CPC ............ H05B 33/0842; H05B 33/0833; H05B 33/0893; H05B 37/0272
  (Continued)

(56) References Cited

U.S. PATENT DOCUMENTS 6,870,325 B2  3/2005  Bushnell et al.
7,132,805 B2  11/2006  Young
(Continued)

FOREIGN PATENT DOCUMENTS

CN  203134324 U  8/2013
CN  103634982 A  3/2014
(Continued)

OTHER PUBLICATIONS

Day, Michael et al., "TLC5940 Dot Correction Compensates for Variations in LED Brightness", Texas Instruments Incorporated, Analog Applications Journal, Analog and Mixed Signals, 4Q, 2005, 4 pages.
(Continued)

*Primary Examiner* — Thuy Vinh Tran
(74) *Attorney, Agent, or Firm* — Phillips, Ryther & Winchester; Justin Flanagan

(57) ABSTRACT

An adjustable LED lighting system includes a plurality of LEDs, at least one driver, and a programmable signal generator to control a drive frequency. The signal generator includes a clock, an input module to receive commands for driving the LEDs, and a frequency adjustment module to drive the frequency of the one or more LEDs. The LEDS are driven at a target or specified frequency for a time period that is specified with a start time and/or an end time. The LED lighting system allows for a variable frequency of outputs during different time periods and/or in response to specific use commands. The LED lighting system includes one or more target frequencies for one or more target time periods. The LED lighting system stores the target frequencies and target time periods and make the frequency modifications at the user-specified times.

19 Claims, 22 Drawing Sheets

Related U.S. Application Data continuation-in-part of application No. 15/089,930, filed on Apr. 4, 2016, now Pat. No. 9,565,733, which is a continuation of application No. 14/941,239, filed on Nov. 13, 2015, now Pat. No. 9,313,856, which is a continuation of application No. 14/615,287, filed on Feb. 5, 2015, now Pat. No. 9,204,524.

(60) Provisional application No. 62/347,180, filed on Jun. 8, 2016, provisional application No. 61/950,676, filed on Mar. 10, 2014.

(51) Int. Cl.

| | |
|---|---|
| *F21V 29/67* | (2015.01) |
| *F21V 29/76* | (2015.01) |
| *F21V 29/83* | (2015.01) |
| *F21V 29/51* | (2015.01) |
| *A61N 5/06* | (2006.01) |
| *A01G 7/04* | (2006.01) |
| *A01G 9/20* | (2006.01) |
| *A01K 63/06* | (2006.01) |
| *F21V 29/70* | (2015.01) |
| *F21Y 115/10* | (2016.01) |

(52) U.S. Cl.
CPC ............ *A01K 63/06* (2013.01); *A61N 5/0613* (2013.01); *F21V 29/51* (2015.01); *F21V 29/677* (2015.01); *F21V 29/70* (2015.01); *F21V 29/76* (2015.01); *F21V 29/83* (2015.01); *H05B 33/0854* (2013.01); *H05B 33/0863* (2013.01); *H05B 33/0872* (2013.01); *H05B 33/0893* (2013.01); *H05B 37/0281* (2013.01); *A61N 2005/0626* (2013.01); *A61N 2005/0651* (2013.01); *F21Y 2115/10* (2016.08); *H05B 33/0842* (2013.01)

(58) Field of Classification Search
USPC .............................................. 315/185 R, 291
See application file for complete search history.

(56) References Cited

U.S. PATENT DOCUMENTS

| | | | |
|---|---|---|---|
| 7,436,134 B2 | 10/2008 | Levine | |
| 7,573,210 B2* | 8/2009 | Ashdown | H05B 33/0818 |
| | | | 315/149 |
| 7,635,957 B2 | 12/2009 | Tripathi et al. | |
| 8,138,690 B2 | 3/2012 | Chemel et al. | |
| 8,519,714 B2 | 8/2013 | Harbers et al. | |
| 8,552,659 B2* | 10/2013 | Ashdown | H05B 33/0869 |
| | | | 315/291 |
| 8,686,666 B2 | 4/2014 | Catalano et al. | |
| 8,704,463 B2 | 4/2014 | Lin et al. | |
| 8,723,427 B2 | 5/2014 | Collins et al. | |
| 8,742,673 B2 | 6/2014 | Campbell et al. | |
| 9,204,524 B2 | 12/2015 | Saffari et al. | |
| 9,313,856 B2 | 4/2016 | Saffari et al. | |
| 9,565,733 B2 | 2/2017 | Saffari et al. | |
| 9,907,148 B2 | 2/2018 | Saffari | |
| 2005/0156539 A1* | 7/2005 | Ball | H05B 33/0815 |
| | | | 315/307 |
| 2006/0176303 A1 | 8/2006 | Fairclough | |
| 2007/0133199 A1 | 6/2007 | Lebens et al. | |
| 2008/0074061 A1 | 3/2008 | Chen et al. | |
| 2008/0265799 A1 | 10/2008 | Sibert | |
| 2009/0009362 A1 | 1/2009 | Miller | |
| 2009/0195159 A1 | 8/2009 | Smith et al. | |
| 2010/0277077 A1 | 11/2010 | Pong et al. | |
| 2010/0327766 A1 | 12/2010 | Recker et al. | |
| 2012/0319598 A1 | 12/2012 | Lee et al. | |
| 2013/0002143 A1 | 1/2013 | Panaccio | |
| 2013/0006556 A1 | 1/2013 | Nishikawa | |
| 2013/0128561 A1 | 5/2013 | Thomas et al. | |
| 2014/0074434 A1 | 3/2014 | De Lima et al. | |
| 2014/0111090 A1 | 4/2014 | Zhang | |
| 2014/0265926 A1 | 9/2014 | Hu et al. | |

FOREIGN PATENT DOCUMENTS

| | | |
|---|---|---|
| CN | 102150474 A | 4/2014 |
| CN | 103731961 A | 4/2014 |
| CN | 103759232 A | 4/2014 |
| CN | 103807620 A | 5/2014 |
| DE | 19810827 A1 | 9/1999 |
| EP | 1659831 A1 | 5/2006 |
| EP | 2645815 A1 | 10/2013 |
| EP | 2732700 A1 | 5/2014 |
| EP | 2743563 A1 | 6/2014 |
| WO | 2007075143 A2 | 7/2007 |
| WO | 2010035200 A | 4/2010 |
| WO | 2011044341 A | 4/2011 |
| WO | 2012015180 A | 2/2012 |

OTHER PUBLICATIONS

U.S. Appl. No. 14/615,287, Non-Final Office Action, dated Aug. 13, 20015, 21 pages.

U.S. Appl. No. 14/615,287, Notice of Allowance, dated Oct. 27, 2015.

U.S. Appl. No. 14/941,239, Notice of Allowance, dated Feb. 19, 2016.

U.S. Appl. No. 15/089,930, Office Action, dated Jul. 12, 2016.

U.S. Appl. No. 15/089,930, Notice of Allowance, dated Nov. 17, 2016.

U.S. Appl. No. 15/377,725, Notice of Allowance, dated Oct. 25, 2017.

\* cited by examiner

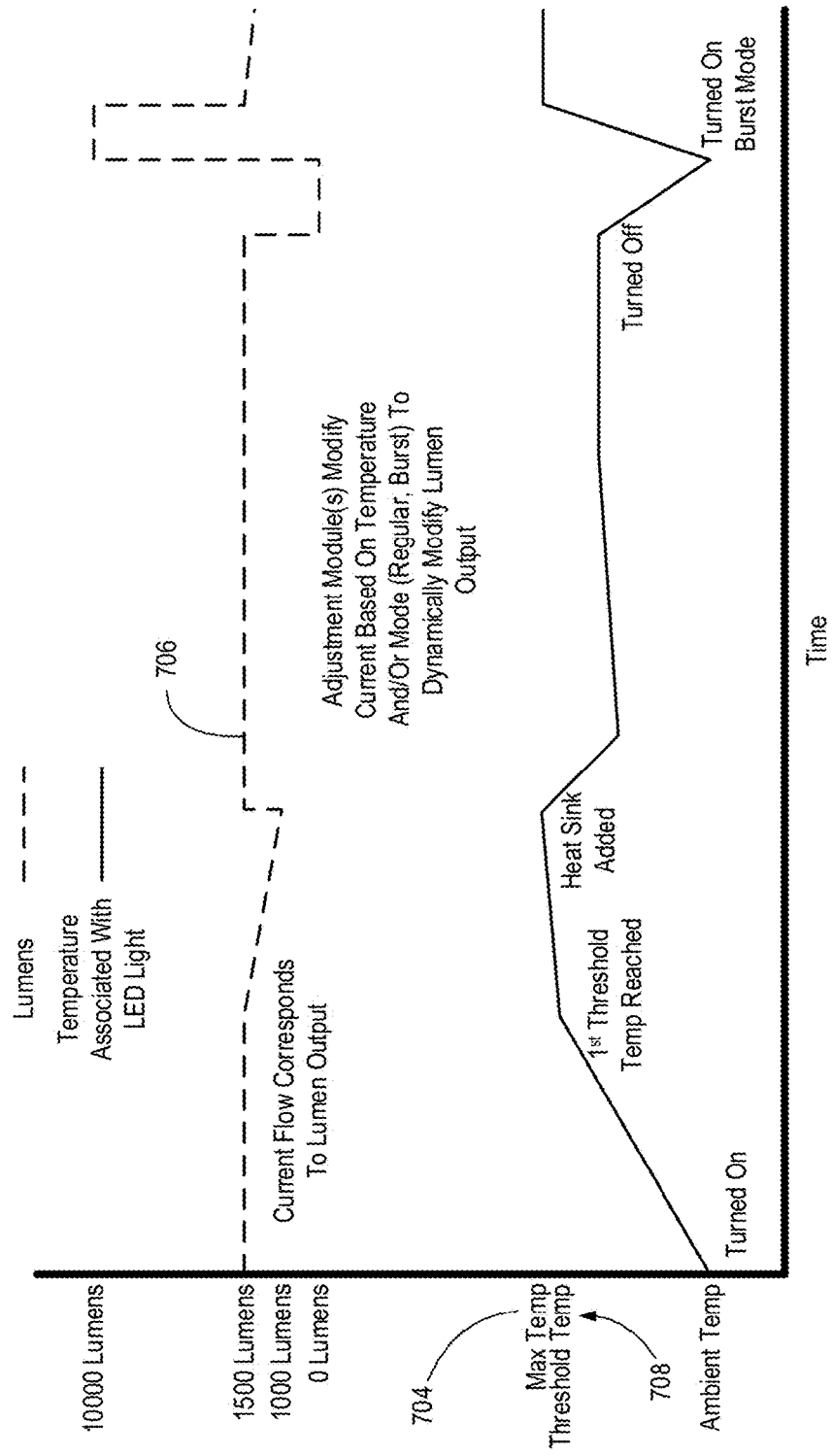

VARIABLE FREQUENCY LEDS AND TIME-BASED FREQUENCY-VARIABLE DRIVERS FOR LED LIGHTING

RELATED APPLICATIONS

This application is a divisional application of U.S. patent application Ser. No. 15/377,725 filed on Dec. 13, 2016, granted as U.S. Pat. No. 9,907,148 on Feb. 27, 2018, titled "LED LIGHTING SYSTEM HAVING AT LEAST ONE HEAT SINK AND A POWER ADJUSTMENT MODULE FOR MODIFYING CURRENT FLOWING THROUGH THE LEDs," which claims the benefit of U.S. Provisional Patent Application No. 62/347,180 filed on Jun. 8, 2016. This application is also a CIP of U.S. patent application Ser. No. 15/089,930 filed on Apr. 4, 2016 (U.S. Pat. No. 9,565,733 granted Feb. 7, 2017), which is a continuation of U.S. patent application Ser. No. 14/941,239 filed on Nov. 13, 2015 (U.S. Pat. No. 9,313,856 granted Apr. 12, 2016), which is a continuation of U.S. patent application Ser. No. 14/615,287 filed on Feb. 5, 2015 (U.S. Pat. No. 9,204,524 granted Dec. 1, 2015), which claims the benefit of U.S. Provisional Patent Application No. 61/950,676 filed on Mar. 10, 2014. Each of the above-identified applications is hereby incorporated by reference in its entirety.

TECHNICAL FIELD

This disclosure generally relates to adjustable (light-emitting diode) LED lighting systems. Specifically, this disclosure relates to the use of LED control systems to mimic exterior conditions, report usage, and/or control light output.

BRIEF DESCRIPTION OF THE DRAWINGS

FIG. 7 illustrates a thermal profile, current flow, and temperature associated with an LED lighting system in various phases, according to one possible usage embodiment.

DETAILED DESCRIPTION

Figure 1A:
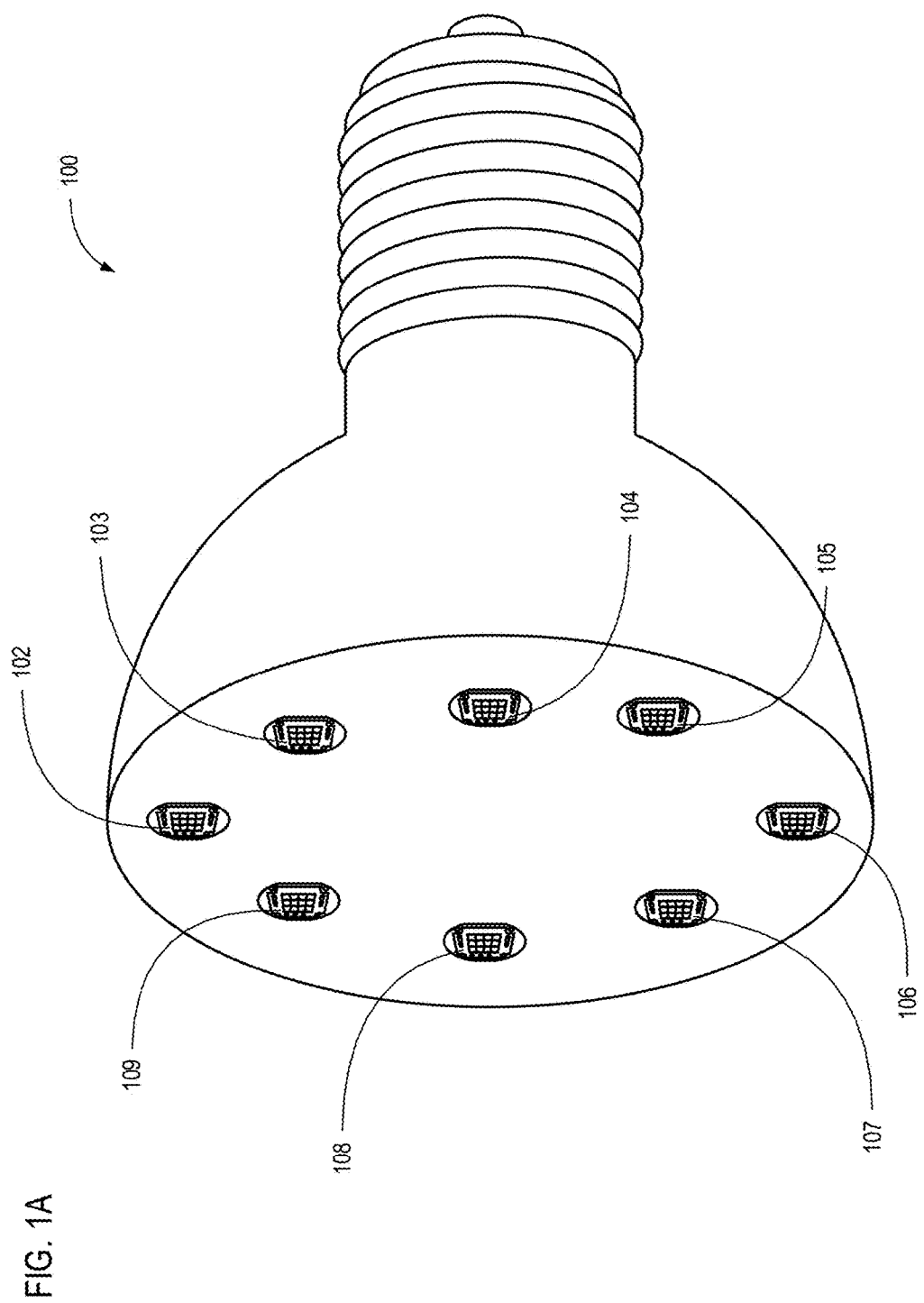
FIG. 1A illustrates a perspective view of an LED light configured for adjustable color and lumen output, according to one embodiment.

Embodiments may include various steps, which may be embodied in machine-executable instructions to be executed by a computer system. A computer system may include one or more general-purpose or special-purpose computers (or other electronic devices). The computer system may include hardware components that include specific logic for performing the steps or may include a combination of hardware, software, and/or firmware.

Embodiments may also be provided as a computer program product including a computer-readable medium having stored thereon instructions that may be used to program a computer system or other electronic device to perform the processes described herein. The computer-readable medium may include, but is not limited to: hard drives, floppy diskettes, optical disks, CD-ROMs, DVD-ROMs, ROMs, RAMs, EPROMs, EEPROMs, magnetic or optical cards, solid-state memory devices, or other types of media/computer-readable media suitable for storing electronic instructions.

Computer systems and the computers in a computer system may be connected via a network. Suitable networks for configuration and/or use as described herein include one or more local area networks, wide area networks, metropolitan area networks, and/or "Internet" or IP networks, such as the World Wide Web, a private Internet, a secure Internet, a value-added network, a virtual private network, an extranet, an intranet, or even standalone machines which communicate with other machines by physical transport of media. In particular, a suitable network may be formed from parts or entireties of two or more other networks, including networks using disparate hardware and network communication technologies.

One suitable network includes a server and several clients; other suitable networks may contain other combinations of servers, clients, and/or peer-to-peer nodes, and a given computer system may function both as a client and as a server. A network may include any number of computers or computer systems. For example, a network may include one or more servers and/or clients. A computer system may include a workstation, laptop computer, disconnectable mobile computer, server, mainframe, cluster, so-called "network computer" or "thin client," tablet, smart phone, personal digital assistant or other hand-held computing device, "smart" consumer electronics device or appliance, medical device, or a combination thereof.

The network may include communications or networking software, such as the software available from Novell, Microsoft, Artisoft, and other vendors, and may operate using TCP/IP, SPX, IPX, and other protocols over twisted pair, coaxial, or optical fiber cables, telephone lines, radio waves, satellites, microwave relays, modulated AC power lines, physical media transfer, and/or other data transmission "wires" known to those of skill in the art. The network may encompass smaller networks and/or be connectable to other networks through a gateway or similar mechanism. Networks may also be wireless and/or be augmented by, replaced by, and used in substitution for point-to-point communication systems and protocols.

Computer systems may include one or more processors and memory. Computer systems may include various input devices and/or output devices. Processors may comprise general-purpose devices, such as Intel, AMD®, or other "off-the-shelf" microprocessors. As used herein, a processor may be a special-purpose processing device, such as an ASIC, SoC, SiP, FPGA, PAL, PLA, FPLA, PLD, or other customized or programmable device. The memory may include static RAM, dynamic RAM, flash memory, one or more flip-flops, ROM, CD-ROM, disk, tape, magnetic, optical, or other computer storage medium. The input device(s) may include a keyboard, mouse, touch screen, light pen, tablet, microphone, sensor, or other hardware with accompanying firmware and/or software. The output device(s) may include a monitor or other display, printer, speech or text synthesizer, switch, signal line, or other hardware with accompanying firmware and/or software.

The computer systems may be capable of using a floppy drive, tape drive, optical drive, magneto-optical drive, or other means to read a storage medium. A suitable storage medium includes a magnetic, optical, or other computer-readable storage device having a specific physical configuration. Suitable storage devices include floppy disks, hard disks, tape, CD-ROMs, DVDs, PROMs, random access memory, flash memory, and other computer system storage devices. The physical configuration represents data and instructions which cause the computer system to operate in a specific and pre-defined manner as described herein.

Suitable software to assist in implementing the invention is readily provided by those of skill in the pertinent art(s) using the teachings presented here and programming languages and tools, such as Java, Pascal, C++, C, database languages, APIs, SDKs, assembly, firmware, microcode, and/or other languages and tools. Suitable signal formats may be embodied in analog or digital form, with or without error detection and/or correction bits, packet headers, network addresses in a specific format, and/or other supporting data readily provided by those of skill in the pertinent art(s).

Several aspects of the embodiments described will be illustrated as software modules or components. As used herein, a software module or component may include any type of computer instruction or computer executable code located within a memory device. A software module may, for instance, include one or more physical or logical blocks of computer instructions, which may be organized as a routine, program, object, component, data structure, etc., that perform one or more tasks or implement particular abstract data types.

In certain embodiments, a particular software module may include disparate instructions stored in different locations of a memory device, different memory devices, or different computers, which together implement the described functionality of the module. Indeed, a module may include a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

Much of the infrastructure that can be used according to the present invention is already available, such as: general-purpose computers, computer programming tools and techniques, computer networks and networking technologies, digital storage media, authentication, access control, and other security tools and techniques provided by public keys, encryption, firewalls, and/or other means.

The features, structures, and operations associated with one embodiment may be applicable to or combined with the features, structures, or operations described in conjunction with another embodiment. In some instances, well-known structures, materials, or operations are not shown or described in detail to avoid obscuring aspects of this disclosure.

Thus, the following detailed description of the embodiments of the systems and methods of the disclosure is not intended to limit the scope of the disclosure, as claimed, but is merely representative of possible embodiments. In addition, the steps of a method do not necessarily need to be executed in any specific order, or even sequentially, nor do the steps need to be executed only once. The terms user, manufacturer, end-user, operator, programmer, and installer are used synonymously in many, if not all, instances of the present disclosure.

In various embodiments, LED lights function as on/off with a specific, single spectrum output. For instance, an LED may be designed to output a certain lumen output and color spectrum.

In some embodiments, an arrangement of LEDs may be used to allow an LED light to be more versatile in the spectrum it is capable of outputting. For instance, the LED light may comprise at least one driver configured to drive an arrangement (e.g., array) of LEDs. A driver may be used to drive the LEDs at various voltages and/or currents in order to change the color temperature of the output light. One or more heat sinks may be configured to cool the LEDs.

In certain embodiments, an LED light features a wireless interface configured to connect with a mobile device and/or server. Further, a processor associated with the LED may be configured for receiving configuration instructions through the wireless interface. Configuration instructions may include, for example, a geographic location. The processor may receive information about the geographic location and adjust the driver to cause the LEDs to mimic a lighting scene from a selected geographic location. The processor may then continuously update the lighting as time passes to mimic changes in the lighting scene from the geographic location. In some embodiments, the processor may be physically connected to or housed along with the LED light. In other embodiments, the processor may be remotely located but still associated with and in communication with a separate microprocessor, microcontroller, or other control interface of the LED light.

The wireless interface may include the use of wireless local area network interface (also known as Wi-Fi™), Bluetooth™, ZigBee™, ethernet, USB™, Long Term Evolution (LTE™), near field communication (NFC), and/or other suitable wireless communication protocol and associated system components.

One or more software, firmware, or hardware adjustment modules may allow a user to program or otherwise select a lighting scene. The LED light may allow the desired lumen output and color spectrum based on the selected lighting scene. For example, a user may desire to grow tomatoes under sunlight from another region of the world. The user may select the other region via software, and the LED light would then mimic the lighting of that other region. As the light changes in the other region, the LED would update its lumen output and color. The new lumen output and color would be representative of the light changes in the other region.

In some embodiments, the selected scene lighting may cause the LED to exceed the normal lumen output during usage. To accommodate these peak usage times of the day, a thermal monitoring module and/or adaptive heat sink may be used.

In some embodiments, LED lights may be either set as "on" or "off" and have a specific, limited lumen output based on the heat sink used. In such embodiments, the current through one or more LEDs in an LED light may be limited based on the heat sink and/or expected or measured operating conditions. An LED light may be fixed at a predetermined lumen output when in an "on" position to prevent one or more portions of the LED light from exceeding a maximum temperature rating associated with one or more components or portions of the LED light. A fixed lumen output may prevent the LED light from exceeding a maximum temperature rating, but may unnecessarily limit the user by preventing the LED light, the power supply, and/or the heat sink from reaching a maximum output.

In some embodiments, a thermal monitoring module may increase the versatility of an LED light allowing it to achieve a maximum lumen output based on measured and/or expected operating temperatures associated with the LED light. In some embodiments, thermal monitoring may be possible via remote programming and/or control, such as via remote programmability through an IP address or direct/wireless connection. Software, firmware, and/or hardware modules may allow an LED light (such as a portable or outdoor LED light) to make real time adjustments to the lumen output based on ambient temperatures; measured, approximated, or estimated LED junction temperatures; and/or other temperatures associated with an LED light.

For example, a 200-watt heat sink may be profiled with 100 high-power LEDs with a light output of 10,000 lumens at 25 degrees Celsius (25c). If an ambient temperature is determined (e.g., estimated or measured) to be −25 c (50 degrees below the profiled 25 c), the adjustment module may increase the power provided to the LEDs within the LED light to increase the lumen output to 50,000 lumens to maintain a desired or maximum temperature set point. As a temperature associated with the LED light, such as a junction temperature, heat sink temperature, surface temperature, ambient temperature, and/or other temperature associated with the LED light, increases, the power provided to the LEDs may decrease, thereby decreasing the lumen output of the LED light. This may allow for a temperature-based increase of the lumen output from one to 10 times in some embodiments, as compared to a fixed-lumen embodiment. Even higher increases in lumen output are possible depending on the configuration, heat sinks, ambient temperature, etc.

If the ambient temperature does not change and the user adds a physical heat sink, the adjustment module may automatically adapt and run the LED with more power to increase the lumen output based on the use-defined or factory settings.

For instance, an LED light without a heat sink may be configured to operate below a maximum temperature by maintaining a fixed-lumen output of 5,000 lumens. The LED light may temporarily increase the lumen output to 15,000 lumens until a temperature threshold is reached, at which point the lumen output may be decreased to the 5,000-lumen output to maintain the temperature below the maximum temperature rating. As described above, the LED light may recognize and/or be told that an external heat sink has been added to the LED light. The heat sink may allow the light output to be increased to 10,000 lumens while still operating under the defined maximum temperature.

In some embodiments, the system may track the operating temperature of the LEDs and determine a life expectancy. For instance, if the LED has a life span of 50,000 hours at an operating temperature of, e.g., 50 degrees Celsius, and a life span of 25,000 hours at an operating temperature of, e.g., 75 degrees Celsius, the system may be able to estimate a remaining lifespan based on the history of the operating temperature of the light source. For example, the system could determine that the LED has operated for 10,000 hours at 50 degrees Celsius and 10,000 hours at 75 degrees Celsius. Based on those numbers, the system may estimate the LED has a life expectancy of 20,000 hours remaining, at 50 degrees Celsius. The system may also estimate the LED life expectancy for other temperatures as well. For instance, the life expectancy may be noted as 20,000 hours at 50 degrees Celsius and 8,000 hours at 75 degrees Celsius. This information could be transmitted to a digital display or through a wireless interface to a mobile device of a user.

In various embodiments, an LED light system may allow for an adjustable lumen and/or color spectrum selection based on user-defined settings. Such a system may be capable of mimicking various lighting scenes. In some embodiments, if a lighting scene requires the LED to surpass a baseline lumen output, the LED may be capable of increasing the lumen output beyond the baseline lumen output based on the ambient temperature, adaptive heat sink profiling, and/or in response to a monitored LED junction temperature. As described herein, the system may also track temperatures and operating hours to determine a remaining life expectancy for the LED.

Systems and methods are contemplated that use any of these features alone or in any combination or permutation. For example, a system may allow for just a variable lumen output, just life expectancy monitoring/reporting, or just color spectrum/intensity adjustability. In other embodiments, one or more of these features may be used in combination. In some embodiments, the spectrum/intensity characteristics may be specified as a histogram of wavelengths or frequencies.

Embodiments may be best understood by reference to the drawing(s), wherein like parts are designated by like numerals throughout. It will be readily understood that the components of the present disclosure, as generally described and illustrated in the drawing(s) herein, could be arranged and designed in a wide variety of different configurations. Thus, the following more detailed description of the embodiments of the systems, methods, and apparatuses is not intended to limit the scope of the disclosure, but is merely representative of possible embodiments of the disclosure. In some cases, well-known structures, materials, or operations are not shown or described in detail.

FIG. 1A illustrates a perspective view of an LED light 100 configured for adjustable color and lumen output. As shown, the LED light 100 may utilize a random array of surface mount LEDs 102-109 to emit light. Each LED 102-109 may be capable of emitting light at various lumen output and/or color spectrums. The color and lumen output of each LED may be controlled collectively by one driver, or the color and lumen output of each LED may be controlled by a separate driver. In another embodiment, unique drivers may drive sets of surface mount LEDs.

In some embodiments, each LED 102-109 may be individually controlled to allow for an adjustment of lumen output, but have a set, unchangeable color temperature (or temperature range based on current output). In such an embodiment, to achieve a specific color temperature, some of the LEDs 102-109 may be utilized at maximum lumen output, some at a partial lumen output, and still others may be left off. Any combination of the LEDs 102-109 may be utilized at any intensity to achieve a desired lumen output and color temperature.

The shape, electrical connection, size, and/or number of LEDs on the LED light 100 are merely illustrative and for discussion purposes only. Any number of LEDs may be grouped together in an LED light, arranged in any pattern or even randomly arranged. For example, an LED light may be rectangular and include a closely arranged two-dimensional array of LEDs.

Figure 1B:
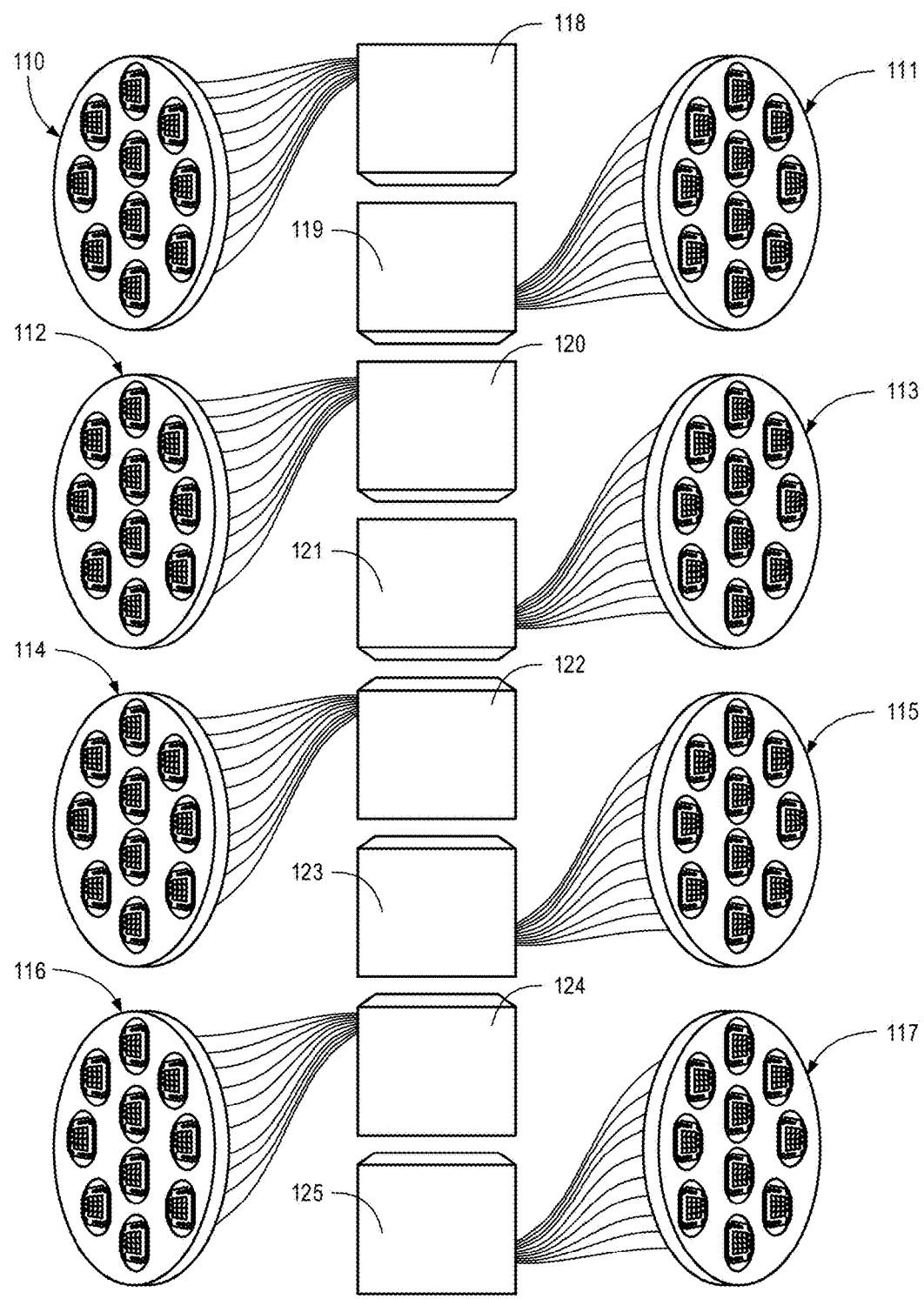
FIG. 1B illustrates eight sets of surface mount LEDs, where each set is connected to a unique driver, according to one embodiment.

FIG. 1B illustrates eight sets of surface mount LEDs 110-117, where each set is connected to a unique driver 118-125. By utilizing multiple drivers, the LED light may be capable of emitting subtle changes in color. For example, a set of surface mount LEDs 110 may be driven by a driver 118 to emit a certain color. At the same time, a second set of surface mount LEDs 111 may be driven by a second driver 119 to emit a different color and/or spectrum. The number of uniquely driven LEDs may determine the resolution of light color and/or spectrum that may be achieved by an LED light system.

Again, the shape, electrical connection, size, and/or number of LEDs on the LED light or on each set of LEDs 110-117 are merely illustrative and for discussion purposes only. Any number of LEDs may be grouped together in an LED light, arranged in any pattern, or even randomly arranged. For example, an LED light may be rectangular and include a closely arranged two-dimensional array of LEDs. Subsets of the rectangular array of LEDs may be controlled by unique drivers to allow for variable intensity, color, and/or color temperature.

Figure 2:
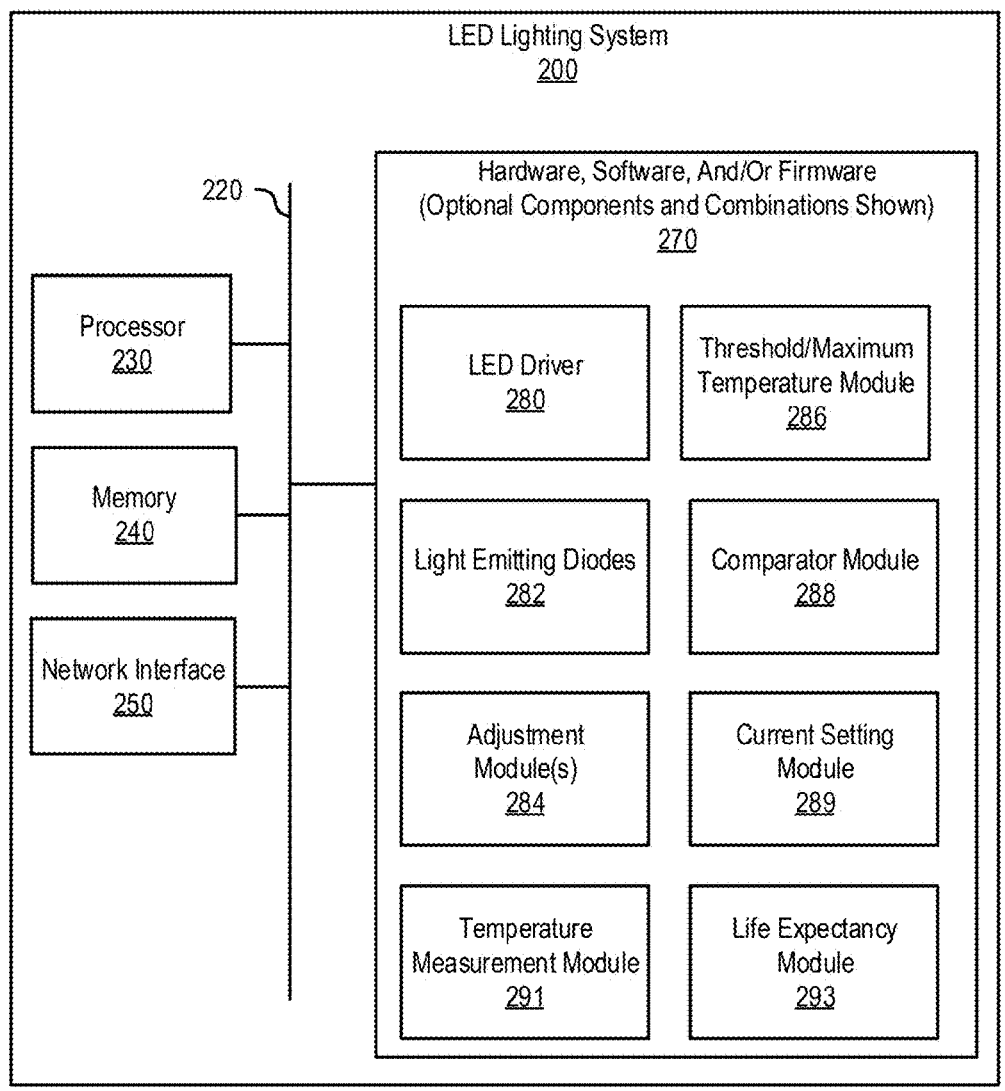
FIG. 2 illustrates a block diagram of an LED lighting system including an adjustment module, according to one embodiment.

FIG. 2 illustrates a block diagram of an LED lighting system 200 including an adjustment module 284. As shown, the LED lighting system 200 may include a processor 230, memory 240, some type of data interface 250, and other optional components 270. A bus 220 may interconnect various integrated and/or discrete components. Various modules may be implemented in hardware, software, firmware, and/or a combination thereof.

These components may allow the LED lighting system 200 to mimic exterior lighting conditions, exceed normal operating lumen output for a certain period of time, and/or provide a life expectancy, as described herein and in any permutation of embodiments.

For example, one or more software, firmware, or hardware adjustment modules 284 may allow a user to program or otherwise select a lighting scene. For instance, the LED lighting system 200 may receive information about an exterior lighting scene through the interface 250. It may then use a comparator module 288 to compare the current lumen output and color spectrum of the LEDs 282 to the lighting scene. An adjustment module 284 may then alter the state of an LED driver(s) 280 and/or a current setting module 289. For example, to increase the lumen output to mimic noonday, the adjustment module 284 may request the current setting module 289 increase the current being provided to one or more LEDs 282.

In various embodiments, the maximum temperature is defined by a maximum temperature module 286. In other embodiments, the maximum temperature is defined or set based on related parameters within the adjustment module 284. The adjustment module 284 may be implemented in software, hardware, and/or firmware. Thus, by way of example only, the maximum temperature may be defined by a circuit-defined current flow, comparator values in hardware or firmware, a measured temperature, or values defined in software.

In some embodiments, a life expectancy module 293 may receive operating temperature data from a temperature measurement module 291 and calculate a life expectancy based on hours used at different operating temperatures. Heat may be monitored by the temperature measurement module 291 from a thermistor and control board to ensure long LED 282 life.

Figure 3:
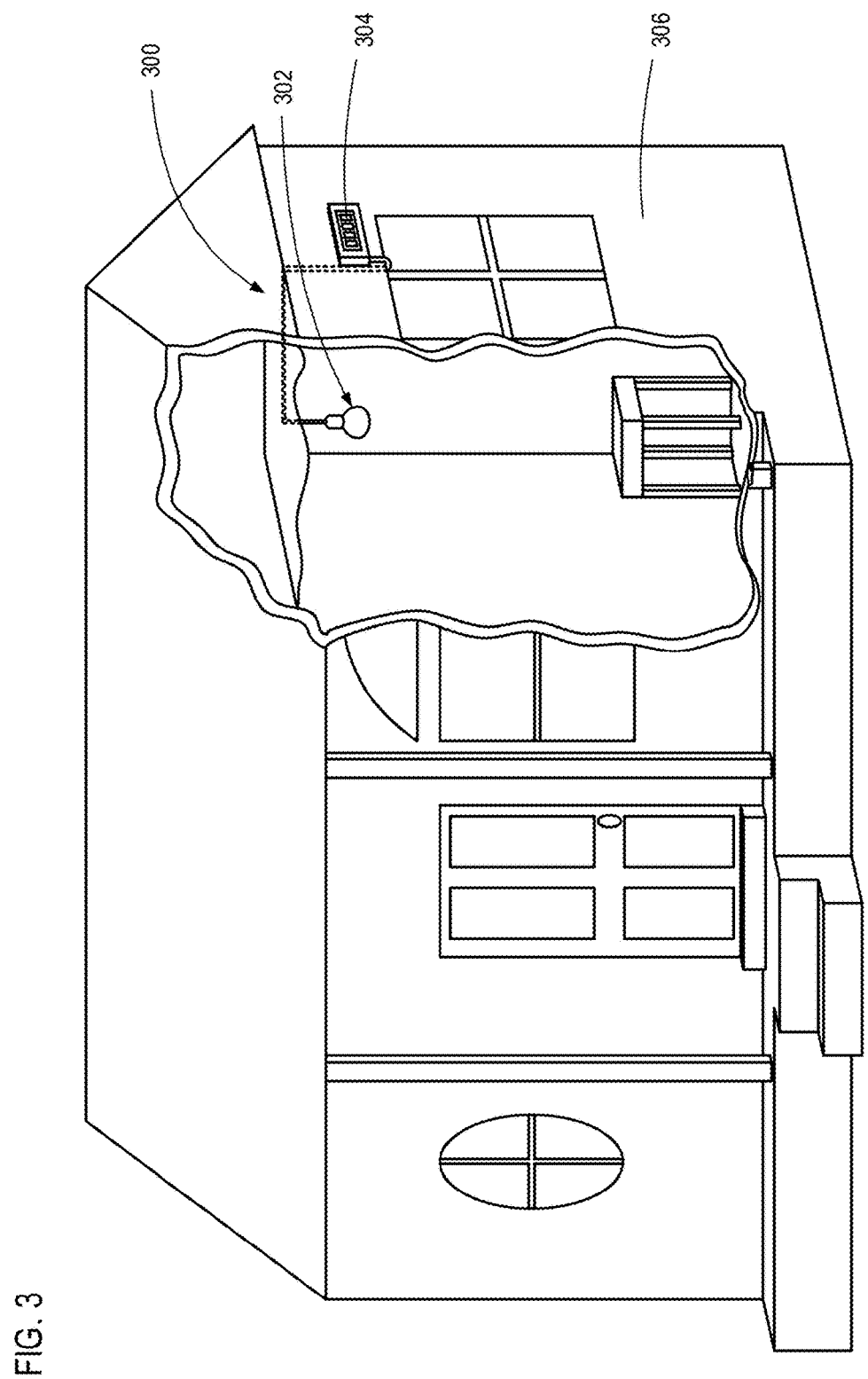
FIG. 3 illustrates an LED lighting system configured to mimic exterior lighting, according to one embodiment.

FIG. 3 illustrates an LED lighting system 300 configured to mimic exterior lighting. As illustrated, an LED light 302 may be configured to receive information from a light meter 304. The LED light 302 may be connected to the light meter 304 via physical wiring, Wi-Fi™, Bluetooth™, or other wireless standards. As illustrated, the LED light 302 may be placed in the interior of a building 306, and the light meter 304 may be placed on the exterior of the building 306 to measure exterior lighting conditions. As the LED light 302 receives information from the light meter 304 (via a wired or wireless connection), the LED light 302 may adjust its lumen output and color spectrum to mimic the exterior lighting. The LED light 302 may have any number of discrete LEDs of any number of colors and/or spectrums. The LED light 302 may have any number of discrete or semi-discrete drivers configured to each drive one or more LEDs.

Figure 4:
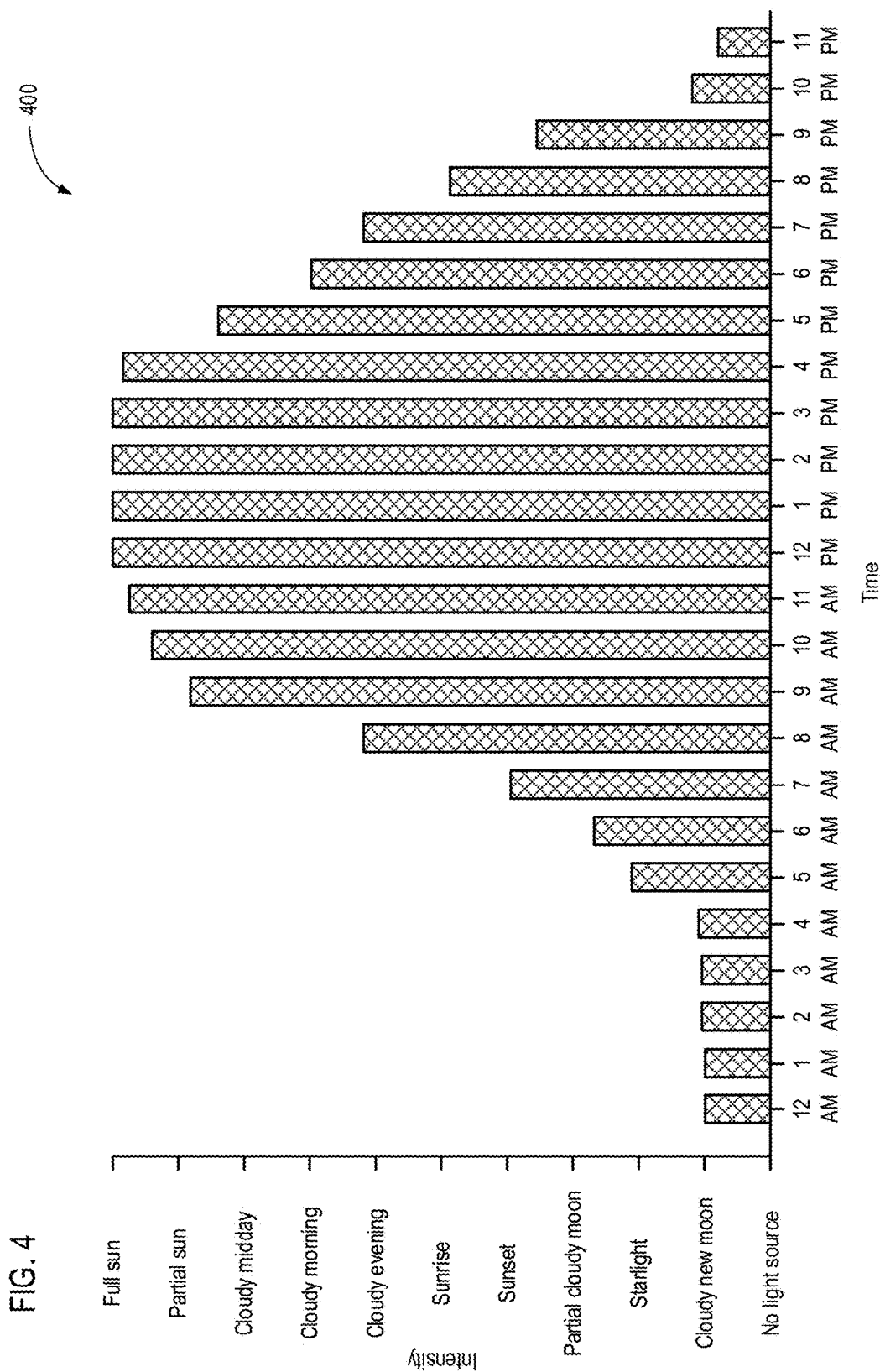
FIG. 4 is a bar graph showing an LED lighting system mimicking a 24-hour day cycle, according to one embodiment.

FIG. 4 is a bar graph 400 showing an LED lighting system mimicking a 24-hour day cycle. The mimicked 24-hour day cycle may be mimicked based on actual light measuring devices, such as the light meter 304 in FIG. 3, or may be based on user-defined or pre-programmed settings.

The bar graph 400 presents time on the x-axis and intensity on the y-axis. During a 24-hour period, the LED light may mimic sunrise, noon, cloud cover, rainstorm, evening, full moon, cloudy moon, partial moon, or other lighting condition. As illustrated, the intensity rises as the brightness of the sun increases. This intensity is representative of an increase in lumen output. In some embodiments, the color temperature may be modified at each interval (or sub-interval) to mimic the color temperature of the 24-hour period as well. For example, the color temperature near sunset at 9 PM might include more red light and/or less yellow light.

In some embodiments, it may be sufficient to mimic the color temperature of a scene; in other embodiments, the actual color of the light may be modified to match that of a specified scene. In still other embodiments, it may be beneficial to mimic or replicate the actual light spectrum distribution of a particular scene.

In order to mimic a certain exterior lighting scene (e.g., noon), it may be necessary to exceed normal operating lumen output for a period of time. The present disclosure provides systems and methods for allowing for variable and/or adjustable lumen output based on the ambient temperature, adaptive heat sink profiling, and/or in response to a monitored LED junction temperature.

In some embodiments, software is used to monitor a temperature associated with a circuit board to prevent overheating. Such software may simply disable the LED light in response to an over-heat signal. In such an embodiment, a variable lumen output LED is not provided.

In other embodiments, the software (or hardware or firmware) not only monitors a temperature, it communicates with the LED light (e.g., an LED driver associated with the LED light) and instructs it to maintain a consistent user-defined or pre-programmed temperature set point. The user can profile the light using constant variables like ambient and LED junction temperature based on the heat sink. In such embodiments, a "smart" profiling system allows for constant temperature set points, variable and/or adjustable lumen output, and/or user-selectable profiles.

One or more software, firmware, or hardware adjustment modules, such as those described in conjunction with adjustment module 284 in FIG. 2, may allow the LED lighting system to prevent overheating while mimicking a lighting scene. The LED light may allow the desired lumen output of a lighting scene based on ambient temperature by choosing a desired temperature set point and the amount of current allowed.

For example, a 200-watt heat sink may be profiled with 100 high-power LEDs with a light output of 10,000 lumens at 25 degrees Celsius (25c). If an ambient temperature is determined (e.g., estimated or measured) to be −25 c (50 degrees below the profiled 25 c), the adjustment module may increase the power provided to the LEDs within the LED light to increase the lumen output to 50,000 lumens to maintain a desired temperature set point. As a temperature associated with the LED light, such as a junction temperature, heat sink temperature, surface temperature, ambient temperature, and/or other temperature associated with the LED light, increases, the power provided to the LEDs may decrease, thereby decreasing the lumen output of the LED light. This may allow for a temperature-based increase of the lumen output by one to 10 times, or more, as compared to a fixed-lumen output embodiment.

Figure 5:
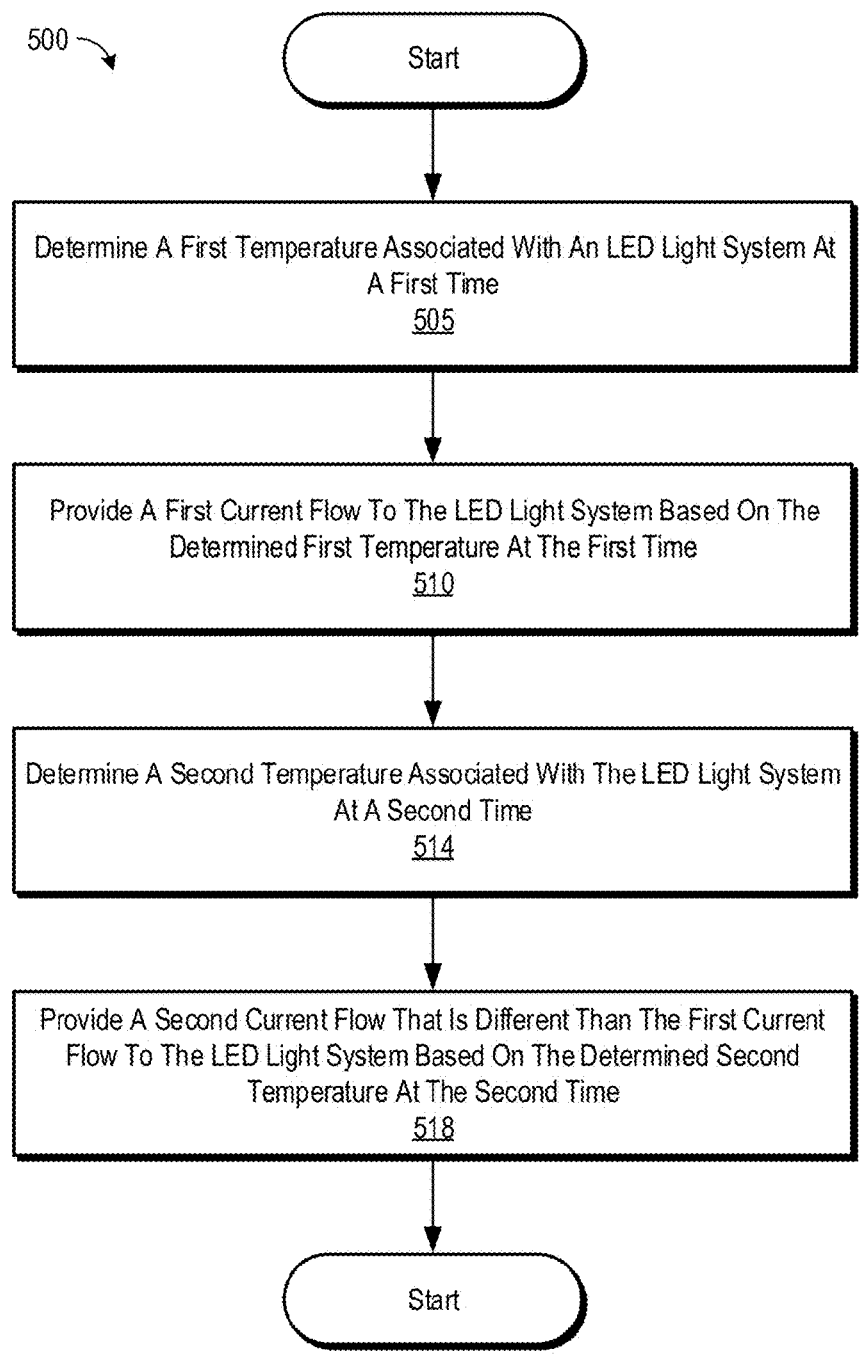
FIG. 5 illustrates a flow diagram of a method for regulating the light output of an LED lighting system, according to one embodiment.

FIG. 5 illustrates a flow diagram 500 of a method for regulating the light output of an LED lighting system, according to one exemplary embodiment. The method steps are provided in no particular order and may be rearranged as would be technically feasible. An adjustment module may determine 505 a first temperature associated with an LED light system at a first time. The adjustment module may provide 510 a first current flow to the LED light system based on the determined first temperature at the first time.

The adjustment module may determine 514 a second temperature associated with the LED light system at a second time. The adjustment module may provide 518 a second current flow that is different from the first current flow to the LED light system based on the determined second temperature at the second time.

Figure 6:
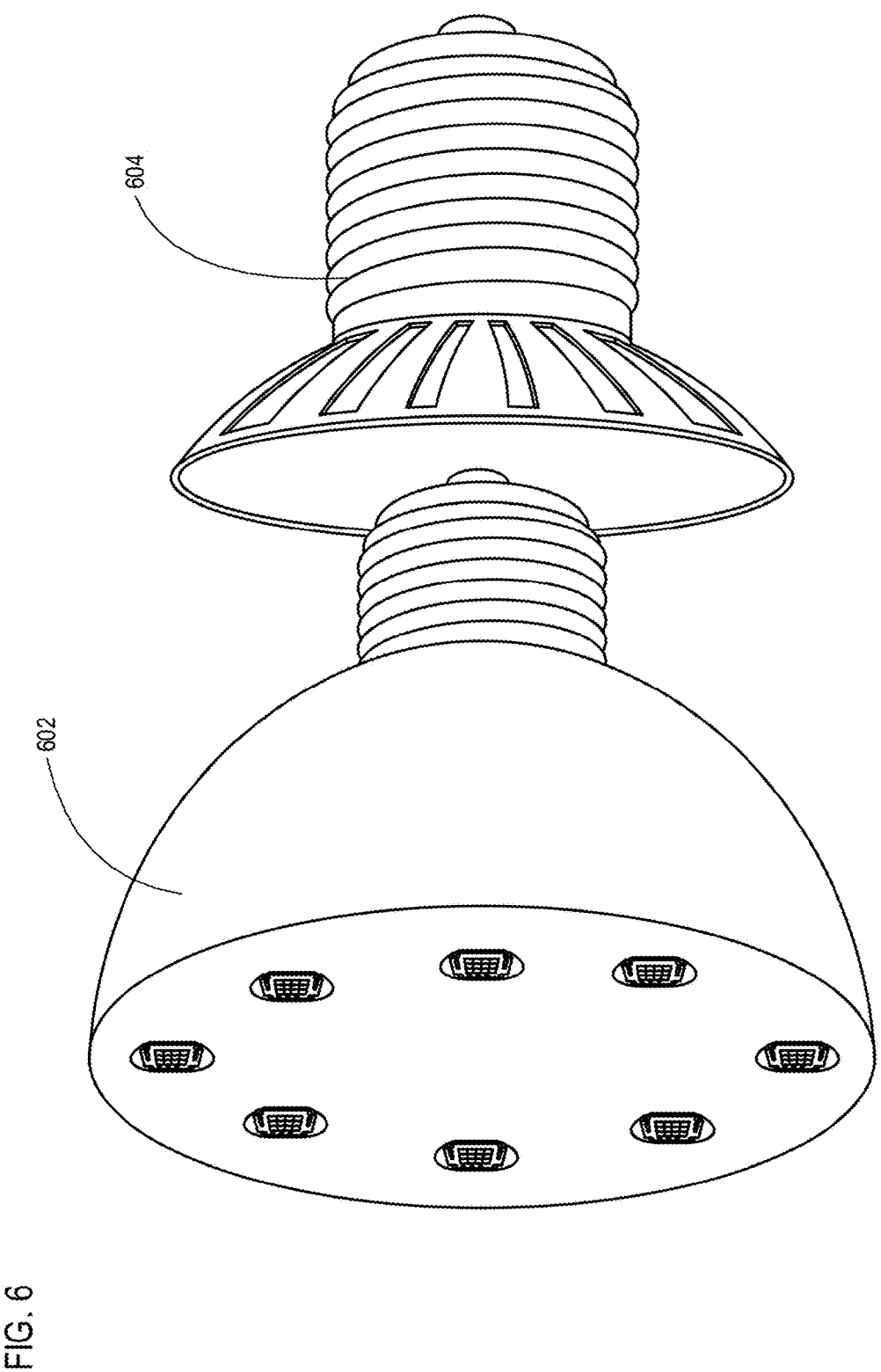
FIG. 6 depicts an LED light and an additional heat sink, according to one embodiment.

FIG. 6 depicts an LED light 602 and an additional heat sink 604. If the ambient temperature does not change and the user adds a physical heat sink 604, the adjustment module may automatically adapt and run the LED light 602 with more power to increase the lumen output based on user-defined or pre-programmed settings. In some constantly monitored embodiments, the addition of the heat sink 604 will lower a monitored temperature and the LED light 602 will automatically increase the lumen output.

For instance, an LED light without a heat sink may be configured to operate below a maximum temperature by maintaining a fixed-lumen output of 5,000 lumens. The LED light may temporarily increase the lumen output to 15,000 lumens until a temperature threshold is reached, at which point the lumen output may be decreased to the 5,000-lumen output to maintain the temperature below the maximum temperature rating. As described above, the LED light may recognize and/or be told that an external heat sink has been added to the LED light. The heat sink may allow the light output to be increased to 10,000 lumens while still operating under the defined maximum temperature.

If additional lumen output is desired, the user could add extra heat sinks on to the existing light by either bolting or magnetically adding extra heat sinks. For example, if the existing heat sink is designed for 100 watts, the user could add another 50 watts to help keep the existing light cool and allow the user to double or at least increase the lumen output again. Modular heat sinking decreases the temperature of the circuit board, thereby allowing increased current flow and associated increases in light output.

In underwater applications, the user could achieve double to triple lumen output. For example, if the user had the light running at 85 c underwater, the water would help cool the heat sink and a new profile defined by the module (potentially software, firmware, or hardware) would increase the lumen output. In such embodiments, the water would act as an additional heat sink, which could be used to increase the amount of current than can be provided to the LED light without exceeding a temperature threshold. The increase in current flow would allow for increased lumen output for the user.

An LED adjustment module may automatically detect the heat sinks, detect heat sinks based on a measured temperature associated with the heat sink, and/or explicitly be made aware of the modular heat sinks manually by a user or automatically through an electrical, mechanical, and/or electromechanical communication system.

FIG. 7 illustrates an example of a thermal profile 702, current flow 706, and temperature associated with an LED lighting system in various phases, according to one possible usage embodiment. As shown, various events may be used to keep the temperature of the LED light below a certain maximum temperature 704 while the LED light is emitting increased lumen output.

As illustrated, when the light first turns on, the LED light may emit additional lumen output. For example, in FIG. 7, the lumen output of the LED light begins at 1,500 lumens. After the LED light exceeds a first threshold temperature 708, the current flow may be decreased to prevent the LED light from overheating. This decrease in current may be a gradual change or may be an abrupt decrease.

Once an additional heat sink is added, the LED light may maintain the additional lumen output level. Even with the additional heat sink, the temperature of the LED light may still increase. If the temperature does build up and pass the first threshold temperature 708 with the heat sink, the current may still be decreased.

In some embodiments, with temperature monitoring, the light is "smart" and can be programmed to decrease the amount of lumen output while decreasing the amount of heat. The amount of light is now variable and can be increased or decreased according to user-defined set points or preset for automatic adjustment. If additional lumens are desired, the light may be mounted on a tripod or other structure, thereby using modular heat sinking to allow for optimum increased lumen output and power supply usage, without overheating.

The user may have even more control to double or triple lumen output and power supply usage by using a modular heat sink like a base, stand, or similar structure and an external adaptive heat sink that has a specific set point (e.g., first threshold temperature 708) profiled in the software. As the heat sink absorbs heat and cools the LED junction temperature, the lumen output is increased.

In some embodiments, a system may profile whatever heat sink is being used and take into account ambient temperature, which makes the heat sink itself hot or cold. The thermal monitoring module may have a turbo boost feature in which the user may program the LED light to double or quadruple the lumen output for 15-20 minutes, before decreasing the lumen output to remain under a threshold temperature. This feature can, for example, be used in dark spaces that require ample light for a limited amount of time.

At times, users may be restricted on the size of a heat sink due to portability issues. The thermal profile software may accommodate for smaller or larger heat sinks. A larger power supply will allow the user to double lumen output.

Software, hardware, and/or firmware adjustability, manufacturing configuration, and/or user adjustability may be relatively easy to use and understand. For instance, a driver board for an LED light or LED lighting system may be connected to a microcontroller board. The driver board may drive a predetermined or programmed current through the LED lighting system. A microcontroller board may include an ARM chip or the like and allow for programming via a computer or other interface device. In some embodiments, the ARM chip or the like may host an accessible webpage or similar through which a user or manufacturer may program the driver board and/or a related adjustment module. Communication may be, for example, facilitated by a PC via an Ethernet port. A home screen from the microcontroller may be accessible via an Internet browser.

In various embodiments, a user may connect two thermistor wires to an LED board and the software, hardware, and/or firmware will read the value of the thermistor. A table may be used to convert the thermistor reading into a temperature reading. The temperature reading may be used as a control variable and/or displayed to a user, such as via the webpage. In addition to tracking temperature, the software may also track the time and how many hours the light is running. It may also record spikes, overheating, or any other events. An example according to various embodiments is described below:

In some embodiments, thermal monitoring software may be user-defined or pre-programmed. An operator can type in a value of 60 c in the set point menu. The system may use this information to prevent the LED junction temperature from exceeding 60 c or perhaps a range including 60 c (e.g., 58 c to 63 c). The LED light may thereby be configured to achieve a certain lumen output by reaching the 60 c set point for a given ambient temperature. Initially, the LED light may, as an example, draw 4.2 amps to output 20,000 lumens. As the heat dissipation capacity of the heat sink is reached, the LED junction temperature may begin to rise beyond the set temperature of 60 c. Accordingly, the current draw may be decreased, thereby decreasing the light output to, for example, 10,000 lumens.

In one embodiment, the LED light may be able to draw 4.2 amps for the first 30 minutes during which it is able to output 20,000 lumens. After the initially cold heat sink begins to reach its dissipation threshold, the light output may be decreased.

In some embodiments, the set point may vary plus or minus 5c while adjusting current flow. If a small drop in temperature resulted in an increased light output followed shortly by an increase in temperature and corresponding decrease in light output, the light might appear to flicker. Accordingly, allowing a set point range may allow the light to maintain stability to reduce flickering.

Figure 8A:
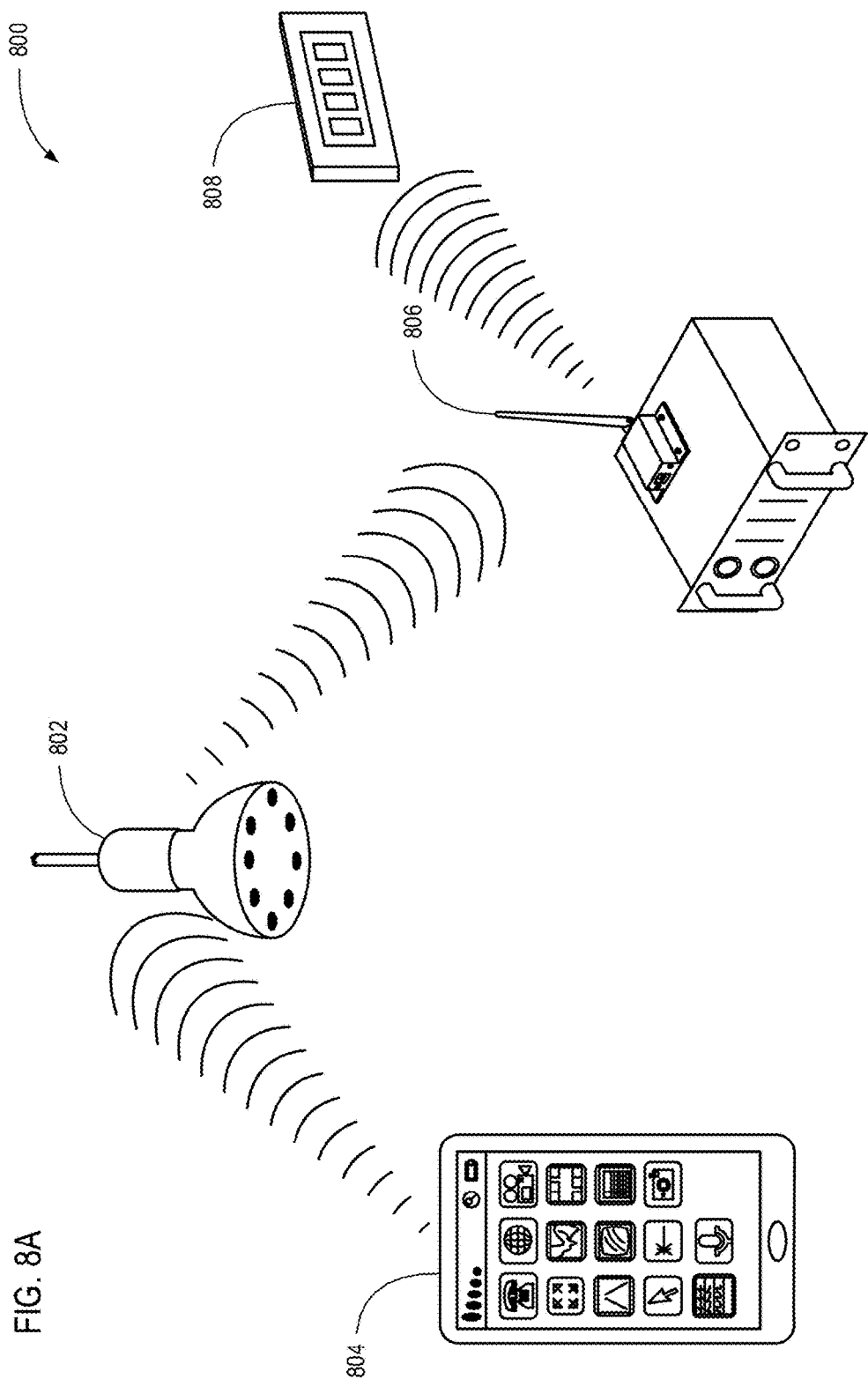
FIG. 8A is a system diagram illustrating a system configured to provide services to an adjustable LED light, according to one embodiment.

FIG. 8A illustrates a system diagram, according to one embodiment, in which a system 800 is configured to provide services to an adjustable LED light 802. The adjustable LED light 802 can communicate with a mobile device 804 and/or a lighting application service 806 via a wireless interface. The lighting application service 806 can include load balancers capable of decryption, application servers, storage, control servers, and/or a logging service (which can include one or more logging servers).

In one example, a user can set up an account with the lighting application service 806 using an application on the mobile device 804. The user registers the adjustable LED light 802 with the lighting application service 806. The lighting application service 806 can store user settings and provide the adjustable LED light 802 with information associated with various lighting scenes. The lighting application service 806 may receive the information concerning a lighting scene from any source, such as a light meter 808 or from a server. For example, the adjustable LED light 802 may be in one region and receive updates via the lighting application service 806 about the lighting spectrum and time zones of another region.

In one embodiment, a user is able to adjust a pre-programmed lighting scene via the mobile device 804. For example, the user may select a lighting spectrum (e.g., color temperature and/or actual wavelength spectrum) from a library of pre-programmed spectrums stored either in the mobile device 804 or in the lighting application service 806. The light may then follow a selected program (e.g., a user might make selections to cause the LED light to mimic the lighting in Oklahoma). In certain instances, a user may customize pre-programmed lighting scenes. For instance, a user may select a tomato plant cycle and elect to add extra blue spectrum in the fourth week of growing to increase yield.

These modified programs can be saved for other experiments and/or shared with others. The modified programs can be emailed or shared on a website provided by the lighting application service 806. This would include any new user-defined spectrum added to the lighting scene. This feature may act as a research and development tool to provide new programs for experimental use for others.

Figure 8B:
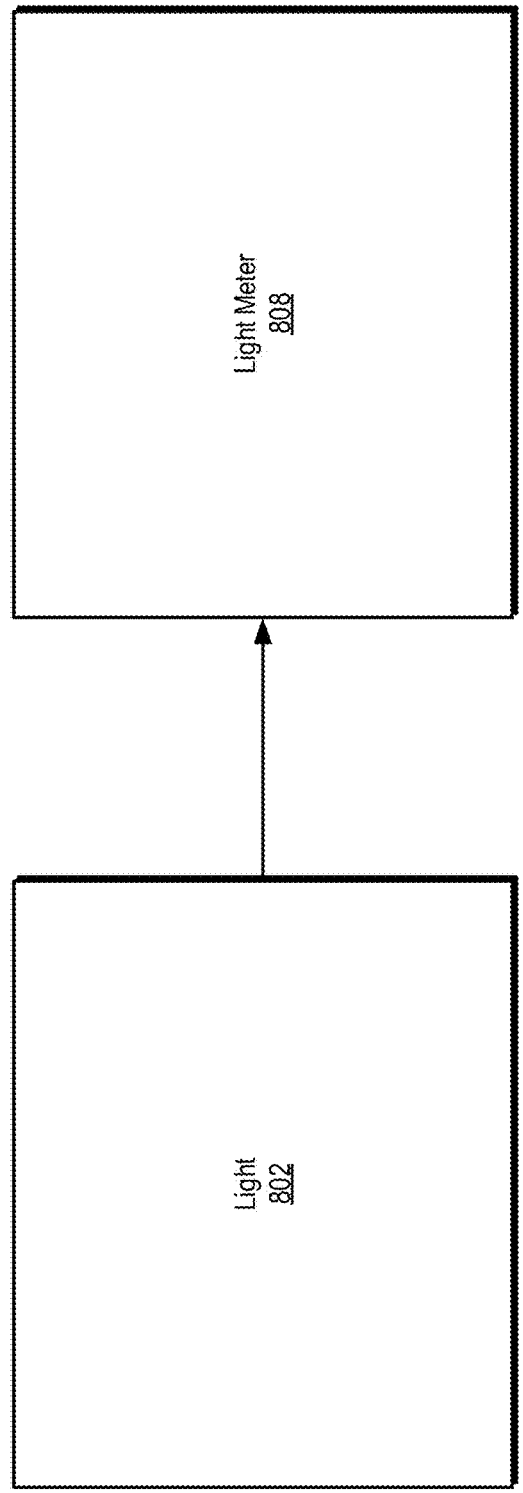
FIG. 8B is a system diagram illustrating a system configured to provide services to an adjustable LED light, according to another embodiment.

FIG. 8B is a system diagram illustrating a system configured to provide services to an adjustable LED light 802, according to another embodiment. As shown, the information concerning a lighting scene may be received directly from a light meter 808 by the adjustable LED light 802. In such an embodiment, the LED light 802 can use the measurements from the light meter 808 and adjust its lighting spectrum to mimic those measurements.

Figure 8C:
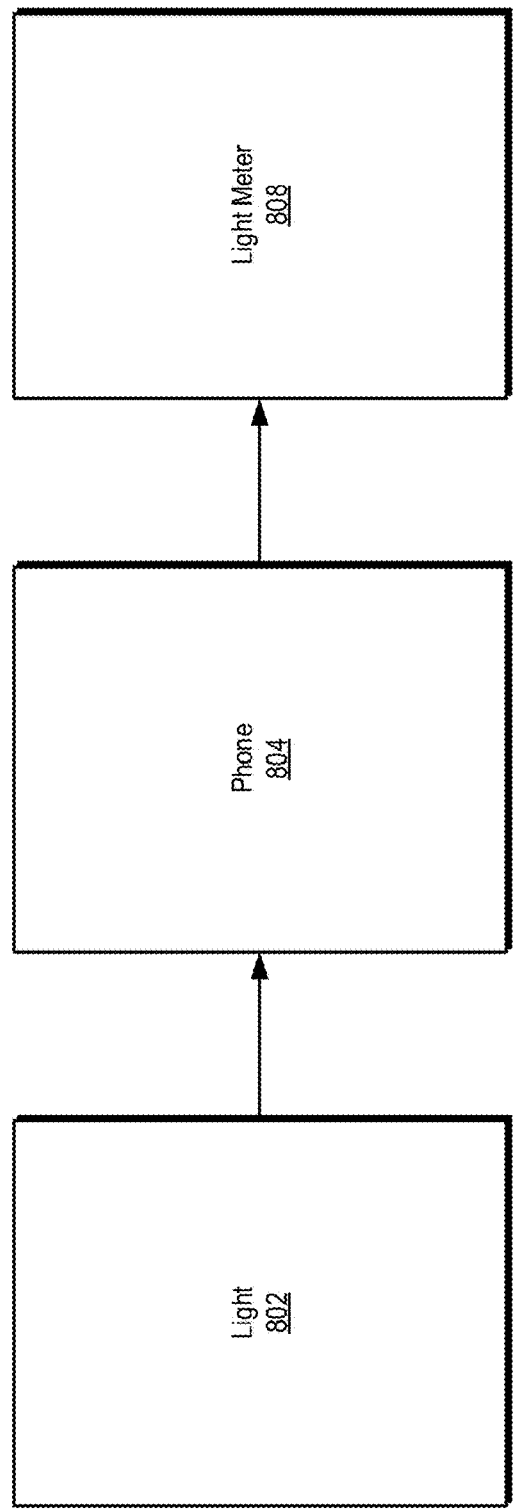
FIG. 8C is a system diagram illustrating a system configured to provide services to an adjustable LED light, according to another embodiment.

FIG. 8C is a system diagram illustrating a system configured to provide services to an adjustable LED light 802 according to a third embodiment. In this example, the mobile device 804 of a user may receive information from a light meter 808, or have a set of pre-programmed lighting scenes. The phone then may instruct the adjustable LED light 802 to mimic the measured spectrum from the light meter 808 or to follow a pre-programmed lighting scene, based on the user selection.

Figure 9:
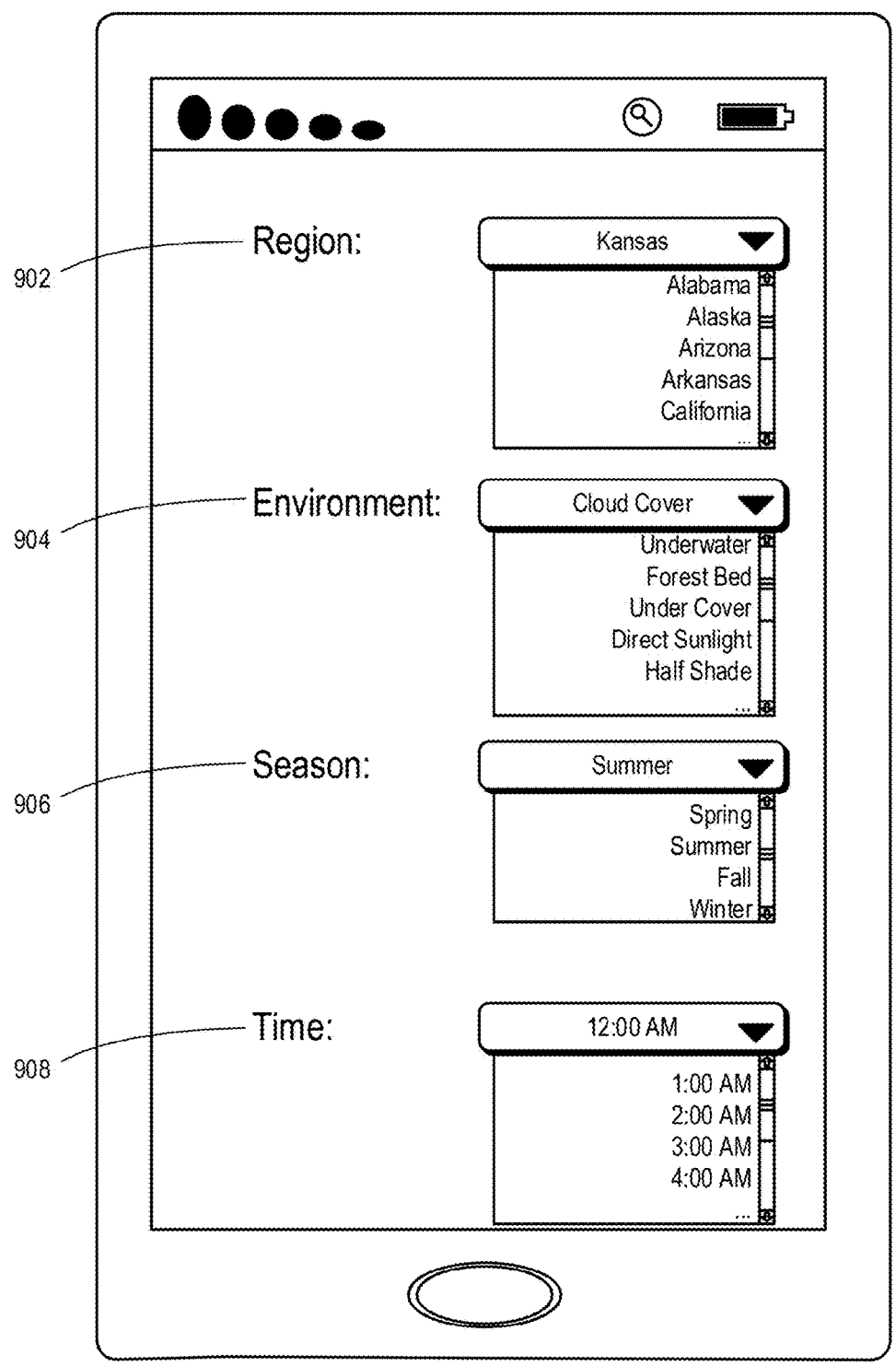
FIG. 9 is an illustration of one possible embodiment of a user interface for selecting a region for an adjustable LED light to mimic.

FIG. 9 is an illustration of a user interface for selecting a region for an adjustable LED light to mimic. In one embodiment, a user can access a settings screen that allows a user to define what lighting a user would like the adjustable LED light to mimic. For example, a region can be selected via a region section 902 of the settings screen 900. The other fields (i.e., 904, 906, 908) may automatically be defined based on the region selection or may be populated based on user preference. The user interface may have several popular light spectrums for the users to choose from (e.g., aquarium, different plant cycles, photography, light therapy, and other needs).

Figure 10:
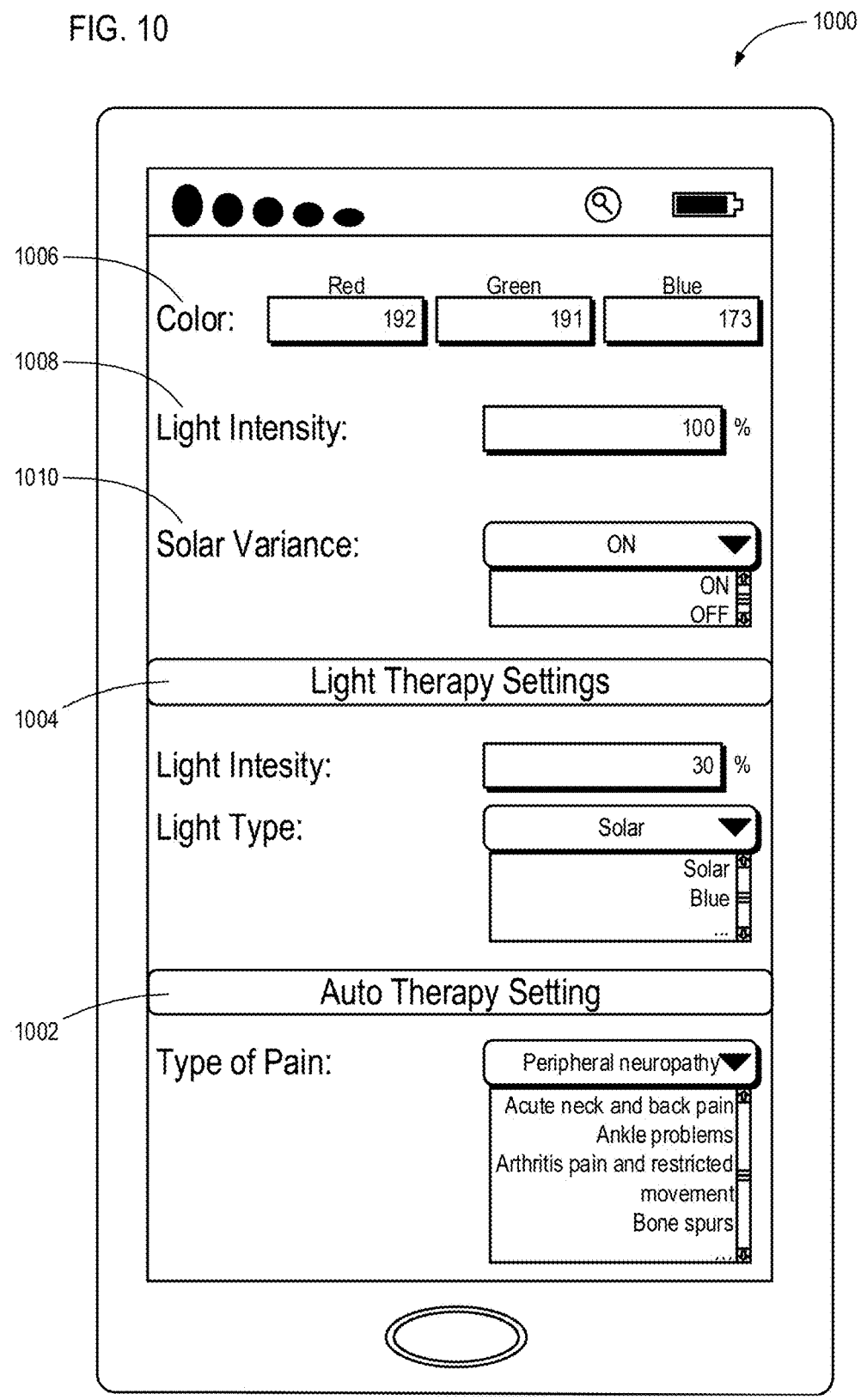
FIG. 10 is an illustration of one possible embodiment of a user interface for selecting light therapy settings for an adjustable LED light.

For example, FIG. 10 is an illustration of an example of a user interface for selecting light therapy settings for an adjustable LED light. As shown, a user may select from several pre-defined settings (i.e., 1002 and 1004) within the light therapy settings screen 1000.

The light may also be manually adjusted via the user interface. The user may adjust the color of the light by way of the color selector 1006. The color selector 1006 may be defined by user-defined RGB values. Sliders or a color wheel may also or alternatively be used. The user can make adjustments to a light intensity selector 1008 by using dimming controls such as knobs or sliding a finger up or down on the touch screen to change the intensities of the whole LED light and/or particular LEDs of the LED light to effectively choose or fine-tune a color spectrum.

The user may also force the LED light to flicker like natural sunlight by turning on a solar variance option 1010. For example, a user selecting this option may cause the adjustable LED light to flicker 5% in light intensity during a short time period. Solar variance may mimic the effects of astronomical scintillation as perceived when sunlight is filtered through clouds, haze, the atmosphere, water vapor, etc.

Figure 11:
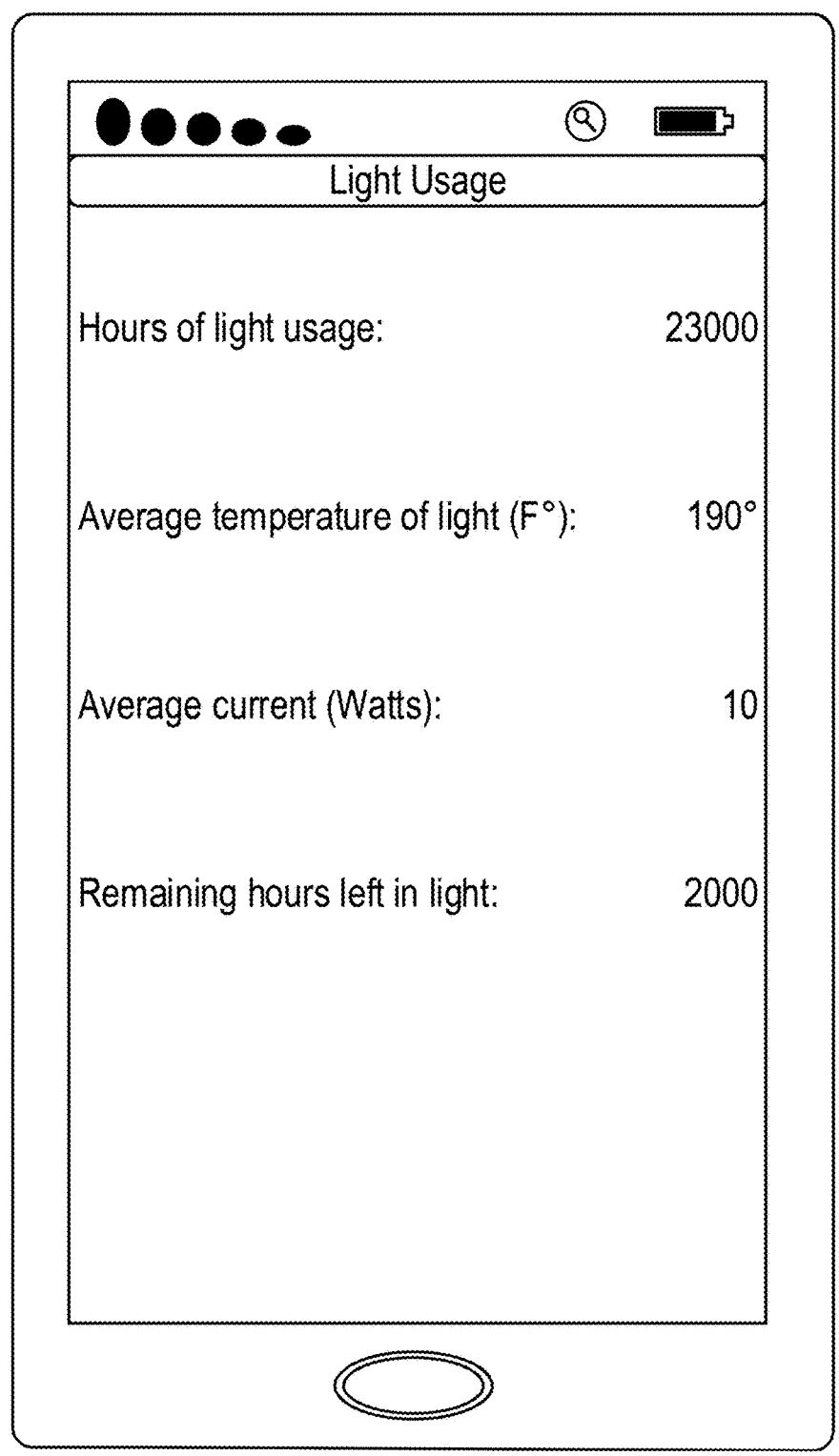
FIG. 11 is an illustration of one possible embodiment of a user interface for displaying light usage and life expectancy of an adjustable LED light.

FIG. 11 is an illustration of a user interface for displaying light usage and life expectancy of an LED light. As shown, a light usage screen 1100 may display hours used at an average temperature. The remaining life expectancy may be estimated and displayed based on the historical usage. This may allow a user to replace a light before it fails.

Figure 12:
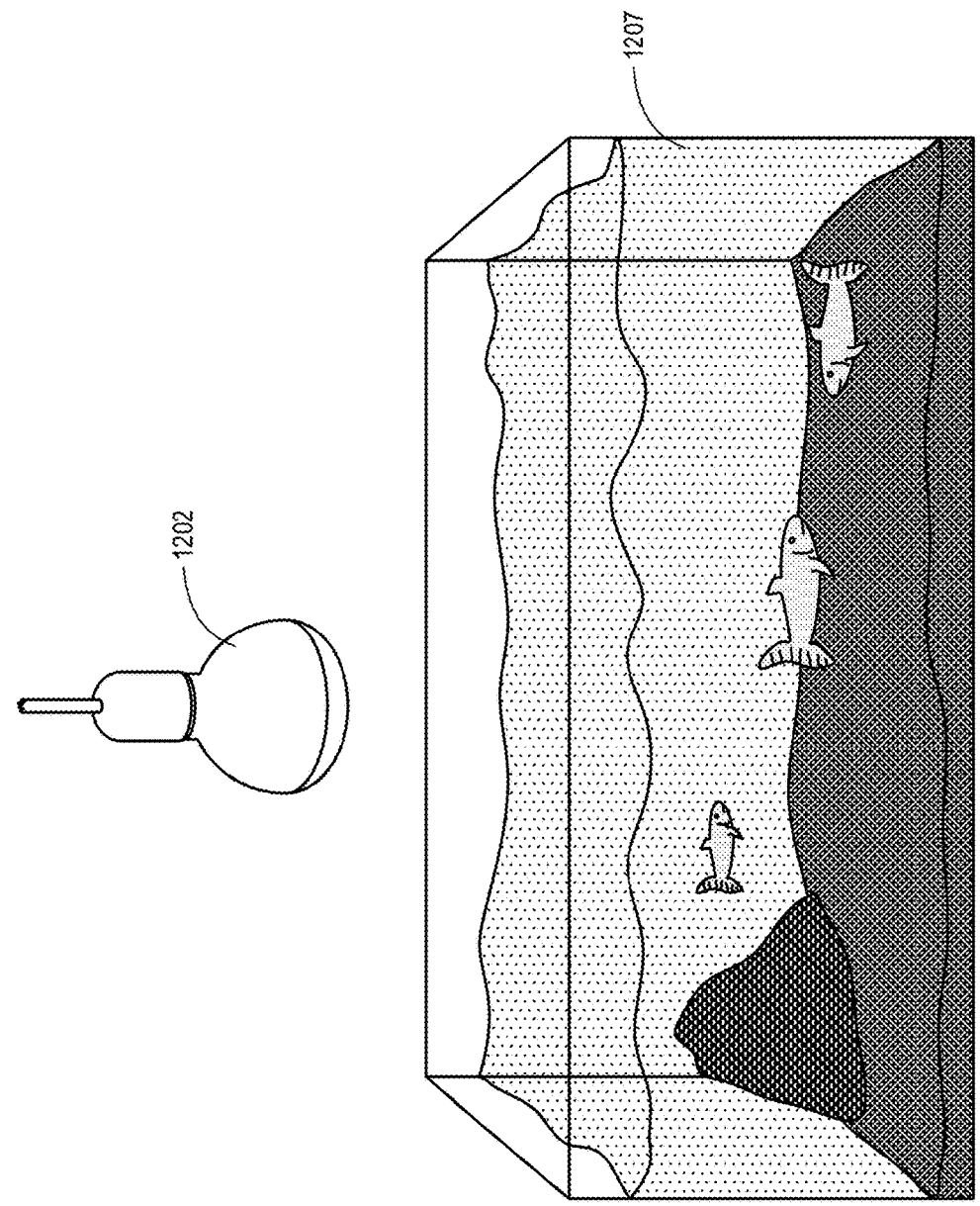
FIG. 12 shows an adjustable LED light installed in an aquarium environment, according to one embodiment.

Adjustable LED lights can be useful in a variety of environments. For example, FIG. 12 shows an adjustable LED light 1202 installed in an aquarium environment 1207. In such an example, certain lighting conditions may be required to maintain the health of the water, fish, plants, and/or other biological conditions. For example, the moonlight and moon phases in a certain region of the world may be critical for the growth of a particular coral. In such a situation, the LED light 1202 may be pre-programmed with or a user may select (manually, electronically, via an online or networked interface, etc.) a lighting scene schedule that corresponds to the moonlight and moon phases.

In some embodiments, a user may make selections that result in the LED light 1202 mimicking a region of the world (either historically or in real time) that corresponds or is correlated with the creatures in the aquarium environment 1207.

Figure 13:
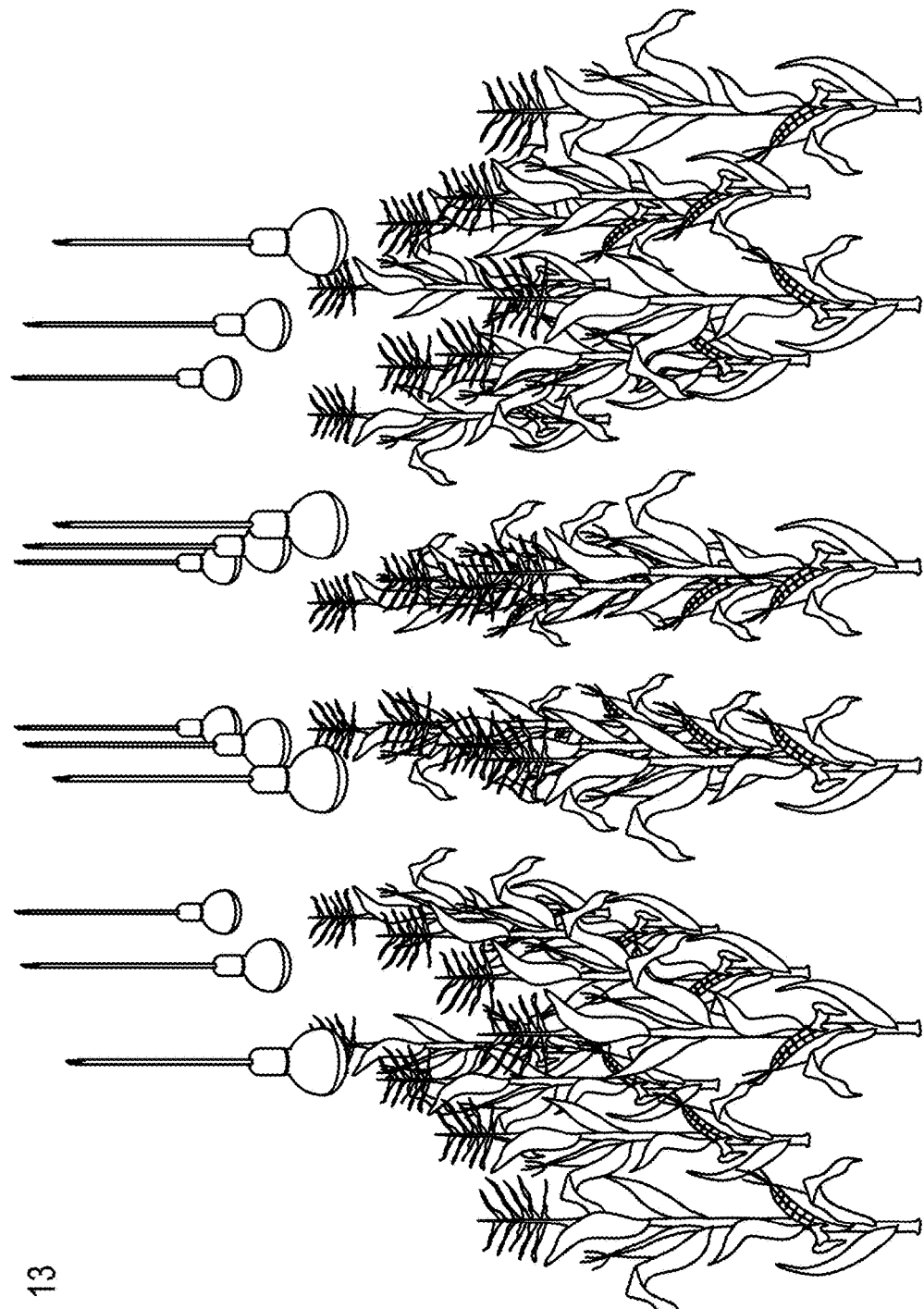
FIG. 13 illustrates a plurality of adjustable LED lights used together in a large facility.

FIG. 13 illustrates several adjustable LED lights networked together in a large facility. The LED lights may be networked together to provide certain lighting scenes to a larger environment. For example, a laboratory may be studying corn growth in different regions. A scientist may use the networked adjustable LED lights to mimic corn growth in a certain region, such as, for example, Kansas. Each light may communicate with a master device (e.g., one of the other light, a computer, or a mobile device), or each may communicate with a server, historical database, real-time monitors, or other system that provides light information for Kansas. It is appreciated that communication, including communication used for programming, monitoring, reporting, and/or other communication, may be performed via wired connections and/or wireless protocols.

The LED lights may follow a schedule (based on historical lighting data, real-time monitored data, and/or a user-defined schedule) for lighting intensity, perceived color, wavelength distribution (spectrum), and/or solar variance. Such LED lights may incorporate the temperature monitoring system that allows for temporary increases in light output and/or modular heat sinks to be used to increase light output permanently or temporarily. The LED light system may also include a monitoring system and monitors the usage of the lights and associated temperatures to determine a life expectancy based on historical usage that includes operating temperatures.

Figure 14:
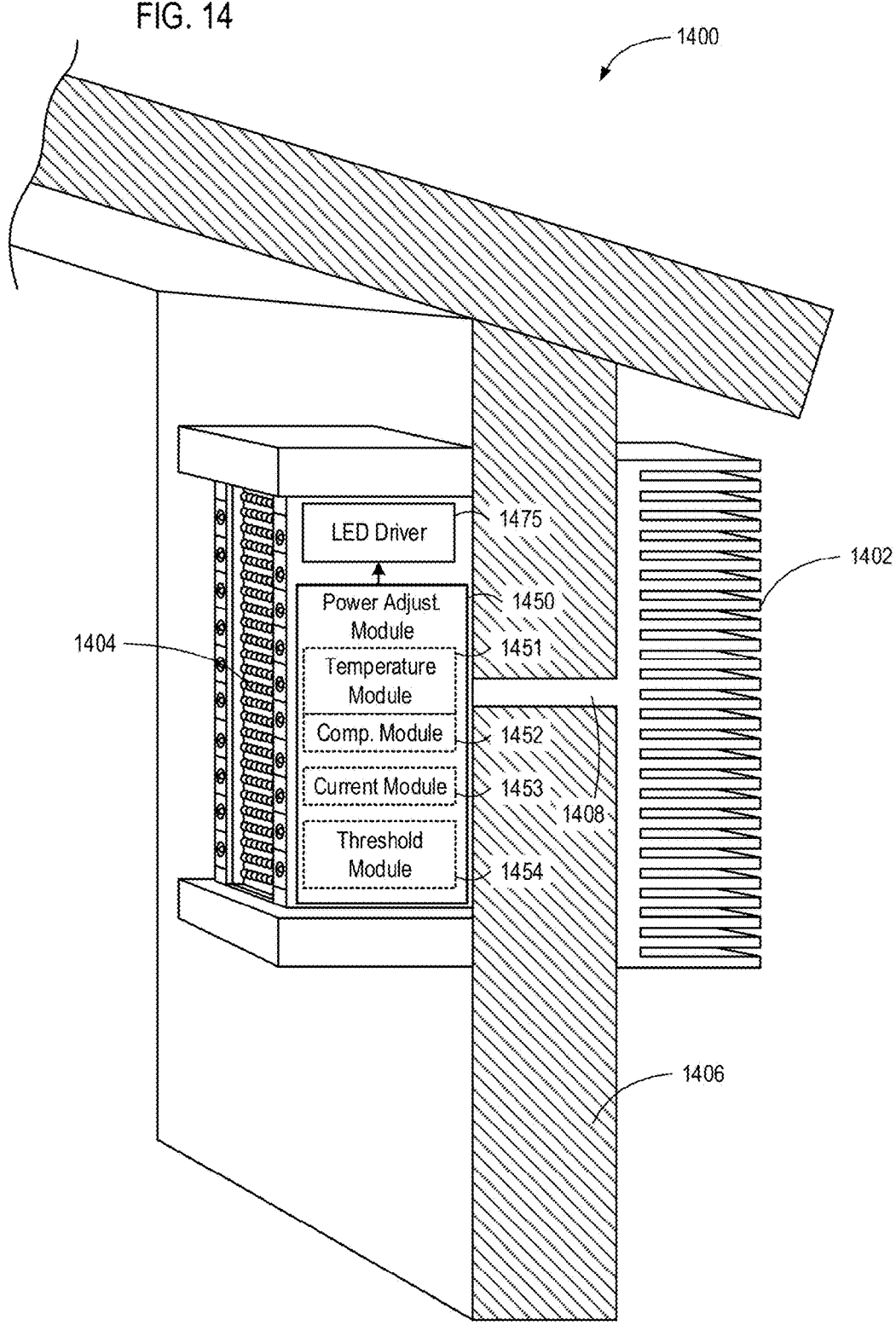
FIG. 14 illustrates an LED lighting system located in a building with a heat sink exterior to the building, according to one embodiment.

FIG. 14 illustrates an LED lighting system 1400 located in a building with a heat sink 1402 exterior to the building. The LED lighting system 1400 may be composed of a plurality of LEDs 1404 and a heat dissipation system.

As shown, a plurality of LEDs 1404 may be located within a space at least partially enclosed by a structural boundary 1406. The enclosed space may be bounded by any of a wide variety of structural boundaries, such as structural boundary 1406, or any other type of structural boundary including, but not limited to, a wall, a roof, a ceiling, a window, soffit, and a fence. The structural boundary 1406 may provide structural support. Alternatively, the structural boundary 1406 may not provide structural support, but still provide a boundary to the enclosed space. For example, the structural support 1406 may be sheetrock, ceiling tiles, cabinets, recessed lighting housing, or trim.

The space where the LEDs 1404 are located may be fully or partially enclosed. In one embodiment, the space may be fully enclosed. For example, the space may be a structure such as a building or room. Alternatively, the space may be a vehicle, such as a bus, airplane, or car. In another embodiment, the LEDs 1404 may be located in a space that is only partially enclosed. Whether partially or fully enclosed, the space may have limited ventilation or otherwise fail to adequately dissipate the thermal energy produced by the LEDs 1404. In some embodiments, the LEDs 1404 may even be recessed in the structural boundary 1406 which would further limit the ventilation of the LEDs 1404.

To dissipate the thermal energy produced by the LEDs 1404 more effectively, the LEDs 1404 may be in thermal communication with the heat dissipation system. The heat dissipation system may comprise a penetrant 1408 and a heat sink 1402. The penetrant 1408 may penetrate the structural boundary 1406 and extend exterior to the at least partially enclosed space. The penetrant 1408 may be in thermal communication with the LEDs 1404 and the heat sink 1402 to conduct thermal energy from the LEDs 1404 to the heat sink 1402. The heat sink 1402 may dissipate the thermal energy conducted by the penetrant 1408.

The penetrant 1408 may include a thermally conductive material. The thermally conductive material may include a metal, a heat-conducting plastic, and/or a ceramic. For example, the thermally conductive material may include copper, aluminum, silver, and/or gold. The penetrant 1408 may include only one thermally conductive material. Alternatively, the penetrant 1408 may include a composite or alloy comprising more than one thermally conductive material. In some embodiments, the thermally conductive material may also be an electric insulator to prevent an electric short from damaging the heat dissipation system or the structural boundary 1406.

The penetrant 1408 may also include a thermally insulated material. The thermally insulated material may provide support for the penetrant 1408. Using thermally insulated material to provide support may lower the cost of the penetrant 1408 and increase the thermal conductivity of the penetrant 1408. For example, the penetrant 1408 may comprise an inexpensive plastic core coated with copper. Because the penetrant 1408 is primarily plastic, the cost would be significantly less than a penetrant of the same size composed of only copper. Also, the surface area of the copper may be increased inexpensively by making the plastic core thicker. As the surface area of the thermally conductive material increases so will the thermal conductance of the penetrant 1408. In some embodiments, the thermally insulated material may provide insulation between the thermally conductive material and structural boundary 1406. By insulating the conductive material, the heat dissipation system may limit thermal excitation of the area surrounding the LEDs 1404.

The penetrant 1408 may extend to an exterior wall, as shown, or it may extend through the structural boundary 1406 to a different interior space. For example, the penetrant 1408 may go through the drywall of a room to a heat sink located in a crawl space or in a space between studs or rafters. The different interior space may also be another room or a space specifically designed for the heat sink. A space designed for a heat sink may include a ventilation system. For example, a heat dissipation system may include heat sinks positioned within the ventilation duct network of a residential or commercial building. In some embodiments, a fan associated with the ventilation system may aid in cooling the heat sinks within the ventilation ducts.

In various embodiments, the heat sink 1402 is positioned exterior to the enclosed space to dissipate the thermal energy produced by the LEDs 1404. The ability of the heat sink 1402 to dissipate the thermal energy produced by the LEDs 1404 is crucial in extending the life of LEDs in situations with limited ventilation. By placing the heat sink exterior to the enclosed space the ability of the heat sink 1402 to dissipate thermal energy may increase.

The heat sink 1402 may be designed based on the enclosed space. The heat sink 1402 may be one common heat sink for all of the LEDs 1404. Alternatively, two or more heat sinks 1402 may dissipate the thermal energy from the LEDs 1404. The heat sink 1402 may be placed in a shaded place to limit solar thermal energy from entering the heat dissipation system.

The LED lighting system 1400 may also include a power adjustment module 1450 to modify a current flow used to drive the LEDs 1404 via an LED driver 1475 to maintain a thermal temperature associated with the LED lighting system 1400 below a maximum or target value. The power adjustment module 1450 may include a temperature module 1451 to determine a temperature associated with the LED lighting system 1400 and a comparator module 1452 to compare the temperature with the maximum value. For example, in some embodiments the power adjustment module 1450 may comprise a thermometer and a comparator circuit. A current module 1453 may be used to set the current flow to a first value based on the determined temperature being below the maximum value. A threshold module 1454 may be used to decrease the current flow to a second, lesser, non-zero value based on the determined temperature being within a predetermined range of the maximum value.

In some embodiments, the power adjustment module may also have a memory to store historic temperature data and a prediction module. In such an embodiment, the prediction module could predict the temperature at certain times during the day based on the stored historic temperature data. For instance, at the hottest part of the day the heat sink 1402 may not be capable of dissipating much heat from the LEDs 1404. To protect the LEDs 1404 from reaching or exceeding the maximum or target temperature, the prediction module may predict when the hottest time of the day will be, and the power adjustment module may lower the current at a time before the predicted time.

The prediction module may be used to adjust the how close the temperature is able to get to the maximum temperature before adjusting the current during a time period. For example, at night the heat sink 1402 may be capable of dissipating more thermal energy because the ambient temperature is lower. The prediction module may predict the lower temperatures and communicate a new predetermined range to the threshold module that is smaller than the previous predetermined range.

In another embodiment, the LED system 1400 can determine when the heat sink 1402 is too hot to dissipate heat. The LED lighting system 1400 may include a thermal switch to decouple the LEDs 1404 from the heat sink 1402 when the heat sink 1402 reaches a certain temperature to prevent a reverse flow of thermal energy that would increase the temperature of the LEDs 1404.

Figure 15:
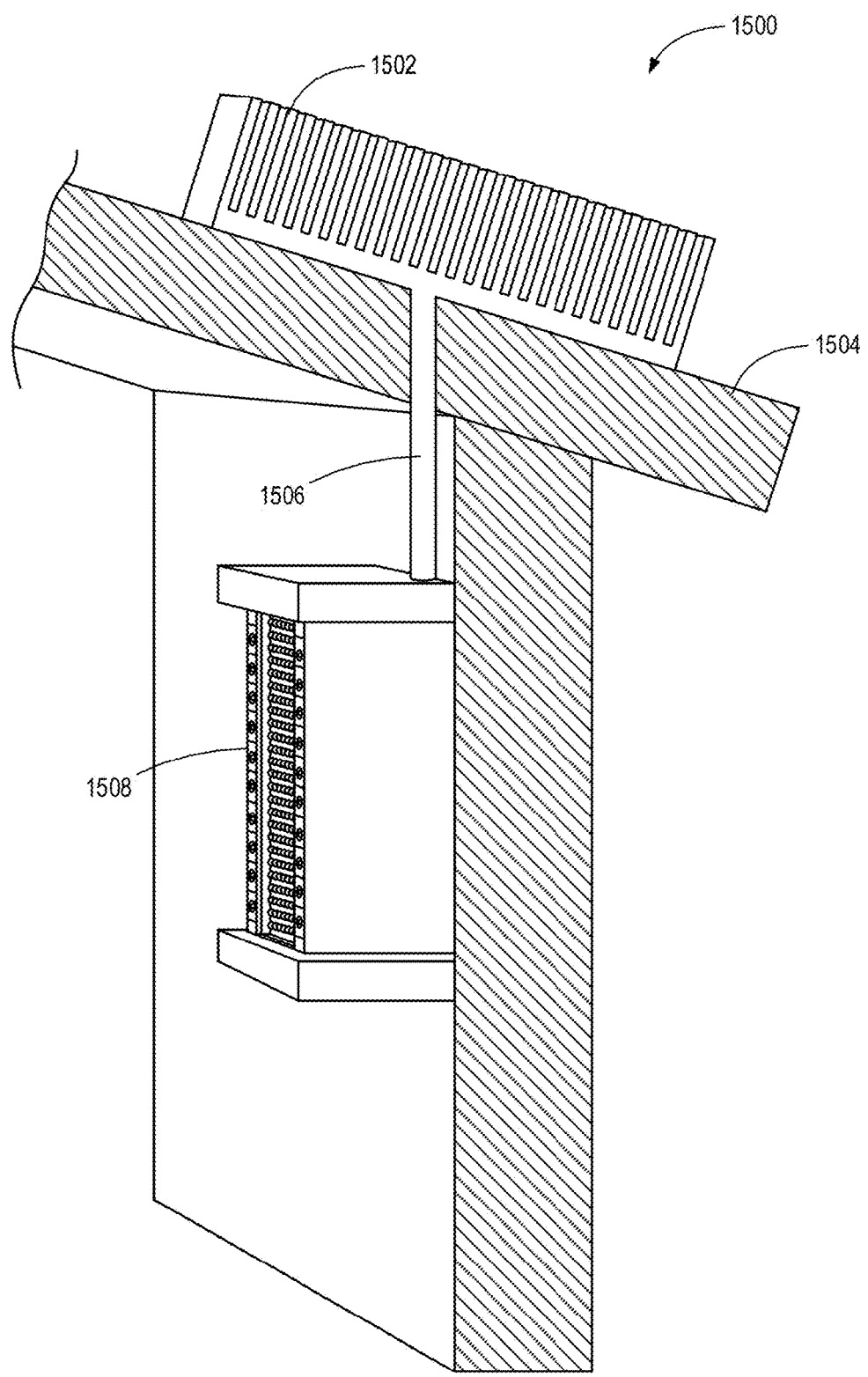
FIG. 15 illustrates an LED lighting system located in a building with a heat sink placed on the roof of the building, according to one embodiment.

FIG. 15 illustrates an LED lighting system 1500 located in a building with a heat sink 1502 placed on a roof 1504 of the building. As shown, a penetrant 1506 may extend through the roof 1504 to thermally couple the heat sink 1504 to the plurality of LEDs 1508.

In some embodiments, the penetrant 1506 may be an existing component in a building. For example, the penetrant 1506 may be a water pipe in a water system. In another embodiment, the penetrant 1506 may be used to conduct the heat to a water heater. As another example, the LED heat dissipation system may utilize an existing component of a heating system within a building as the penetrant 1506. For example, the LEDs 1508 may connect to a heating duct that can then be coupled to the heat sink 1502. In another embodiment the penetrant 1506 may be a heating system itself. For example, the penetrant 1506 may be wound under a floor to provide radiant heat. Alternatively, the penetrant 1506 may be a structural element of the building. For instance, the penetrant 1506 may be a beam, rebar, or other metal reinforcements. By using an existing building component as at least a part of the penetrant 1506, a structure may be retrofitted with an LED lighting system 1500 with limited structural damage.

Figure 16:
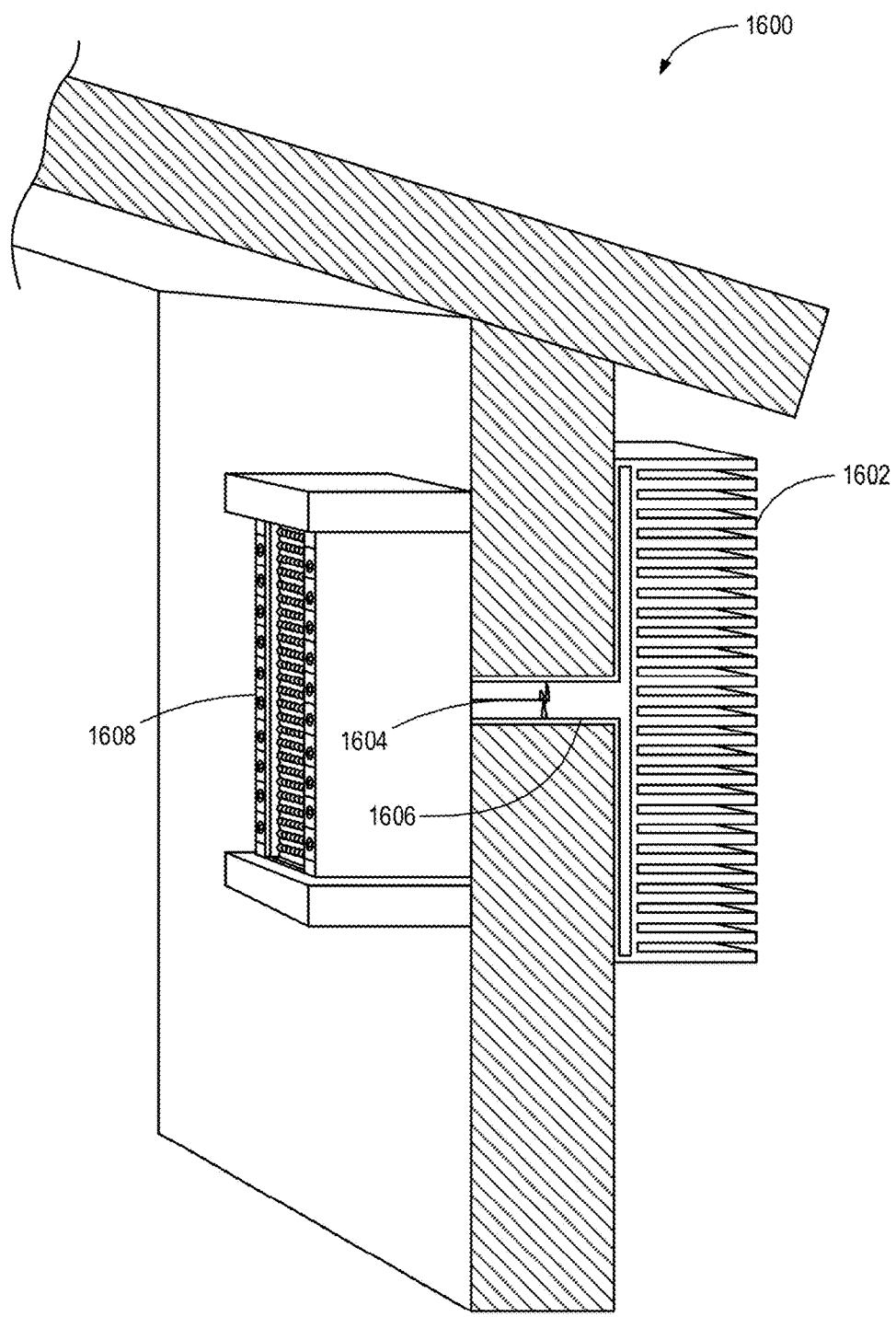
FIG. 16 illustrates an LED lighting system located in a building with a heat sink exterior to the building using a fan to assist in the heat transfer, according to one embodiment.

FIG. 16 illustrates an LED lighting system 1600 using a fan 1604 to assist in the heat transfer from the LEDs 1608 to a heat sink 1602. A penetrant 1606 may be hollow and filled with ambient air, a gas, or a fluid.

In some embodiments, the material in the penetrant 1606 may be actively circulated. For example, as shown the fan 1604 may be used to circulate the material. Air near the heat sink 1602 may assist in the thermal energy dissipation of the heat sink 1602 by absorbing the thermal energy. After a period of time, the air by the heat sink 1602 may become so thermally excited that the thermal energy absorption may slow. The LED lighting system 1600 may detect the slowed thermal energy absorption and turn on the fan 1604 to circulate air in the penetrant 1606.

In another embodiment, the material in the penetrant 1606 may be passively circulated. For example, the penetrant 1606 may have an aperture that induces a stack effect to circulate air. In another example, the penetrant 1606 may be filled with a fluid that is a liquid at normal temperature and pressure (NTP). The liquid may absorb thermal energy produced by the LEDs 1608 causing the liquid to heat up. Once the liquid exceeds NTP, the liquid may transform into a vapor and travel through the penetrant 1606 to the heat sink 1602 where it dissipates thermal energy, condenses, and transforms back into the liquid.

Figure 17:
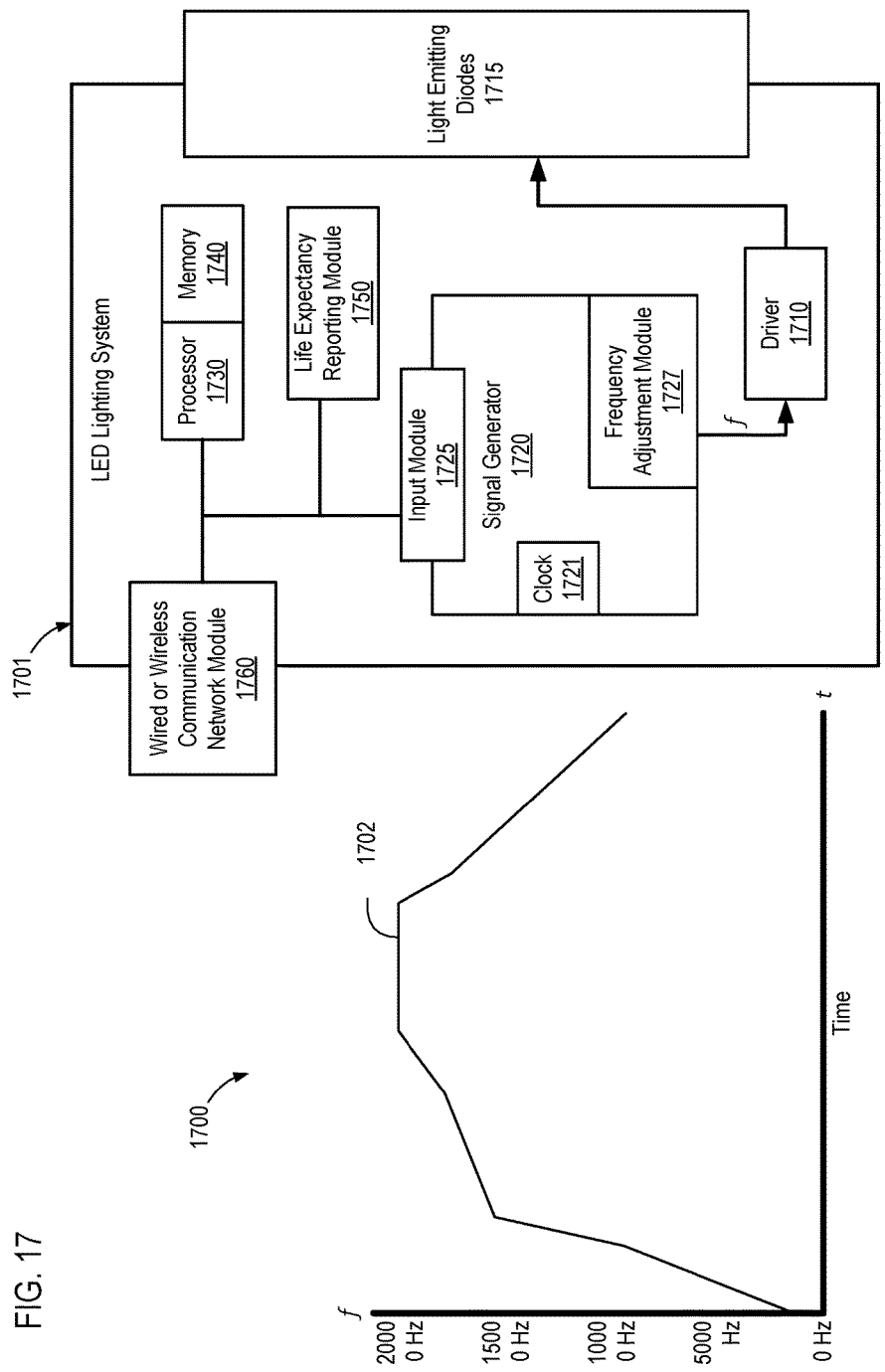
FIG. 17 illustrates an LED lighting system adjusting its frequency over a period of time.

FIG. 17 illustrates an LED lighting system 1701 adjusting its drive frequency 1702 as shown in graph 1700 of frequency, f, over a period of time. An LED lighting system 1701 may have a driver 1710 to drive its LEDs 1715. To drive the LEDs 1715, the driver 1710 may provide an electric current at a drive frequency, f. As shown, the drive frequency 1702 may range from 1 kHz to 20 kHz.

The drive frequency 1702 is the rate at which the drive current oscillates. In some embodiments the LEDs 1715 are driven by a direct current. While direct current traditionally does not oscillate, the direct current may be forced to oscillate between an on and off state creating a pseudo-oscillation. The drive frequency in these direct current embodiments is the rate at which the drive current is forced to pseudo-oscillate.

A programmable signal generator 1720 may control the drive frequency. In some embodiments, the programmable signal generator 1720 may also modify the pulse width of a direct current. The programmable signal generator 1720 may include a clock 1721, an input module 1725, and a frequency adjustment module 1727.

The clock 1721 may be used to keep time. In some embodiments, a user may specify a time for the LED lighting system 1701 to modify the drive frequency 1702. The clock 1721 may determine the current time. The LED lighting system 1701 may compare the current time with the specified time and determine whether it is time to modify the drive frequency 1702. In one embodiment, an external user device may be used as the clock. For example, a cell phone, computer, or other device may be in communication with the LED lighting system 1701 and provide the current time to the LED lighting system. Alternatively, the external user device may also be used to update an internal clock.

The input module 1725 of the programmable signal generator 1720 may receive commands to modify the drive frequency of one or more of the LEDs 1715 to a target frequency during a time period. The frequency adjustment module 1727 of the programmable signal generator 1720 may modify the drive frequency of one or more of the LEDs 1715 to the target frequency during the time period. As in FIG. 2, the LED Lighting system 1701 may include a processor 1730 (230, FIG. 2), memory 1740 (240, FIG. 2), and a life expectancy reporting module 1750 (293, FIG. 2), each of which may communicate or report via wired or wireless communication network module 1760 (data interface 250, FIG. 2 that can be wired or wireless as described herein).

According to one embodiment, the user device may send the command to modify the drive frequency 1702 of the LED lighting system 1701 at the time the user desires to change it. Alternatively, the user device may send the command to modify the drive frequency 1702 of the LED lighting system 1701 before the time the user desires to change it. If the command is sent before the desired change time, the command to modify the drive frequency 1702 of the LED lighting system 1701 may include a target frequency and a target time period. The LED lighting system 1701 may store the target frequency and target time period and make the frequency modification at the user specified time. The input module 1725 may have a storage device to store a plurality of target frequencies associated with a plurality of time periods.

Figure 18:
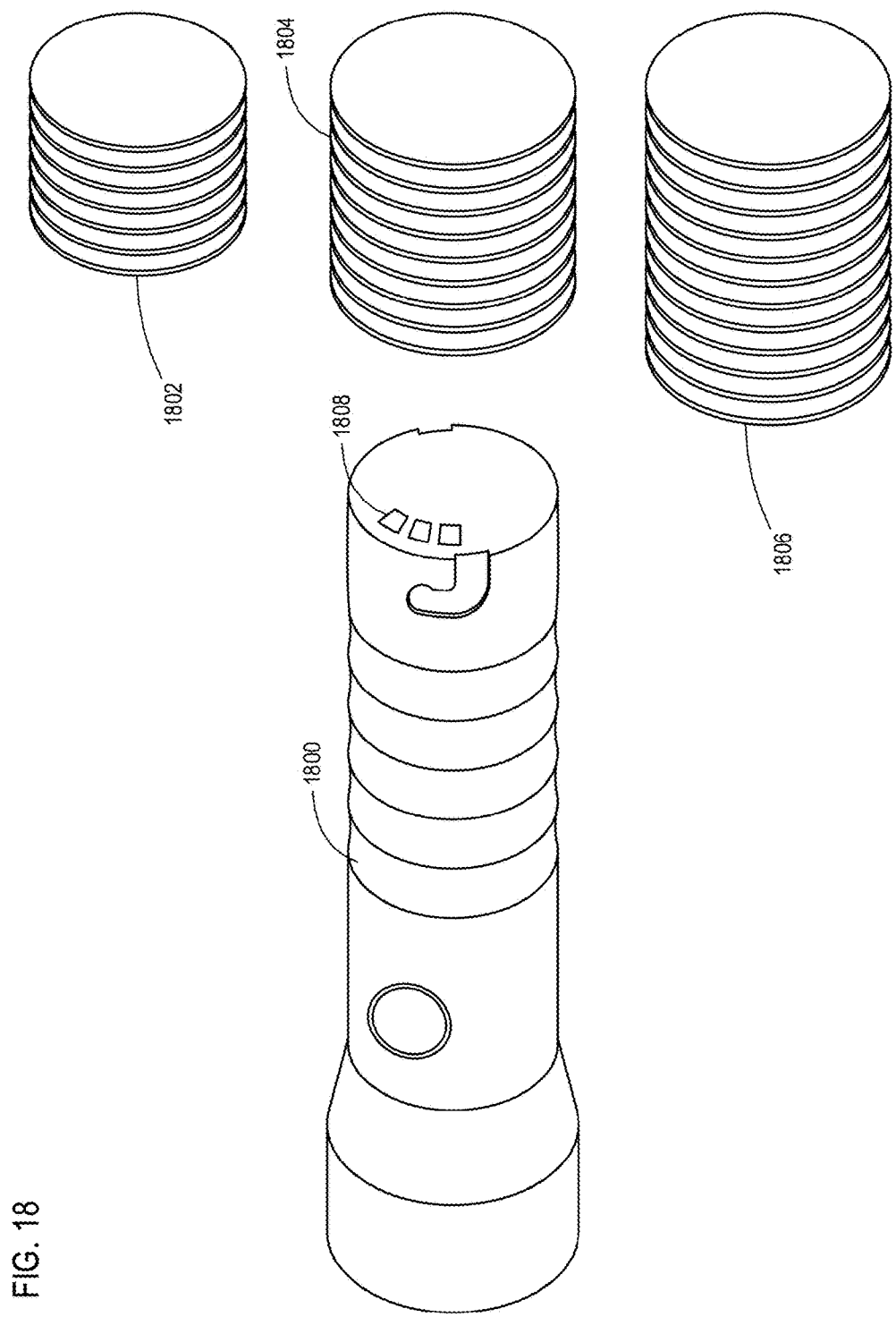
FIG. 18 illustrates an LED lighting system with three smart heat sinks, according to one embodiment.

In another embodiment, the input module 1725 can also receive "use commands" that specify the purpose of the plurality of LEDs 1715 and the input module 1725 can create a target frequency during a time period based on the use commands. For example, a movie theater may have a specific output requirement during movie times such as 20 kHz with a color rendering index of 96-100. A use command may be sent to the input module 1725 indicating the start of a movie. Based on the use command, the programmable signal generator 1720 may adjust the LED drive frequency to 20 kHz. As another example, an LED lighting system 1701 placed outside may receive a use command that causes the programmable signal generator 1720 to modify the drive frequency to a frequency that deters insects. FIG. 18 illustrates an LED lighting system 1800 with three smart heat sinks (i.e., heat sink 1802, 1804, and 1806) according to one embodiment. The LED lighting system 1800 may have varying sizes of smart heat sinks (e.g., 1802, 1804, 1806) that communicate a thermal resistance value associated with the capability of the smart heat sink to dissipate thermal energy to the LED lighting system 1800. A smart heat sink may have an output module that can communicate with an input module 1808 of the LED lighting system 1800.

In some embodiments, the communication between the output module and the input module may be digital. The smart heat sink may have a storage device with the thermal resistance value stored on it. The smart heat sink may digitally communicate the thermal resistance value to the LED lighting system 1800 via a direct connection or wirelessly.

For example, the input module 1808 and output module of the smart heat sink may use Bluetooth™, Wi-Fi™, ZigBee™, NFC, or other wireless communication protocols. In some embodiments, the LED lighting system 1800 may have a magnet and the smart heat sink may have a Hall effect sensor. In such an embodiment, the battery life may be preserved by limiting communication to when the Hall effect sensor detects the magnet.

The smart heat sink may also have a digital chip that receives power when the input module 1808 of the LED lighting system 1800 comes into contact with the output module. For instance, securing the smart heat sink to the LED lighting system 1800 may complete a circuit. The input module 1808 may conduct electricity from the LED lighting system 1800 to the output module of the heat sink. The electricity from the LED lighting system 1800 may power a heat sink battery, communications modules, active elements, or attachments. Active elements may include, but are not limited to fans, battery indicator lights, and/or speakers. In some embodiments, the smart heat sink may also include a power port to charge user devices. For example, the heat sink may have a USB port that can power a cell phone.

In another embodiment, the communication between the output module and the input module 1808 may be analog. For example, the output module of the heat sinks (e.g., 1802, 1804, 1806) may have a plurality of contacts arranged to indicate to the input module 1808 the thermal resistance value. The contacts may be flat electric contacts, or may be a series of pins and holes. As shown, the input module 1808 may consist of three contacts. To indicate the different thermal resistance values, each heat sink may have a different combination of contacts. For example, in the LED lighting system 1800 as shown, the small smart heat sink 1802 may have one contact, the medium smart heat sink 1804 may have two contacts, and the large smart heat sink 1806 may have three contacts. The contacts of the smart heat sink touch some combination of the contacts of the output module when attached. Based on the combination, the input module 1808 recognizes the thermal resistance value of the smart heat sink. For example, if the LED lighting system 1800 detects one contact the LED lighting system 1800 may recognize that the small smart heat sink 1802 is attached.

After the LED lighting system 1800 determines the thermal resistance value stored on it, a power adjustment module may modify the current flow based at least in part on the thermal resistance value associated with the smart heat sink. The current flow may also be based on a combination of the thermal resistance value and the current temperature. For example, the LED lighting system 1800 may have a maximum or target operating temperature. The current may be limited within a certain temperature range of the maximum or target operating temperature. If the attached smart heat sink has a high thermal resistance value, the temperature range may be set to be very close to the maximum or target operating temperature. Whereas, if the attached smart heat sink has a low thermal resistance value, the temperature range may set far from the maximum or target operating temperature.

In one embodiments, a first, larger heat sink may be integrated with a building or vehicle, such that the LED lighting system 1800 may be coupled to the integrated heat sink in a first, high-power (high-heat) state. The LED lighting system 1800 may then be removed from the vehicle or building and used in a portable mode with one or more portable heat sinks of varying sizes. The power driving the LED, and therefore the lighting intensity, may decrease in the portable mode based on the heat sink used. FIG. 18 illustrates three heat sinks 1802, 1804, and 1806 that can be selectively coupled with LED lighting system 1800. In some embodiments, more than one heat sink can be coupled at the same time. For example, the heat sinks 1802, 1804, and 1806 may be configured to attach to one another and communicate which combination of heat sinks have been attached to LED lighting system 1800.

In still further embodiments, the LED lighting system 1800 may have a current profile associated with each heat sink when used out of water and a different (increased) current profile when submerged in water.

Figure 19:
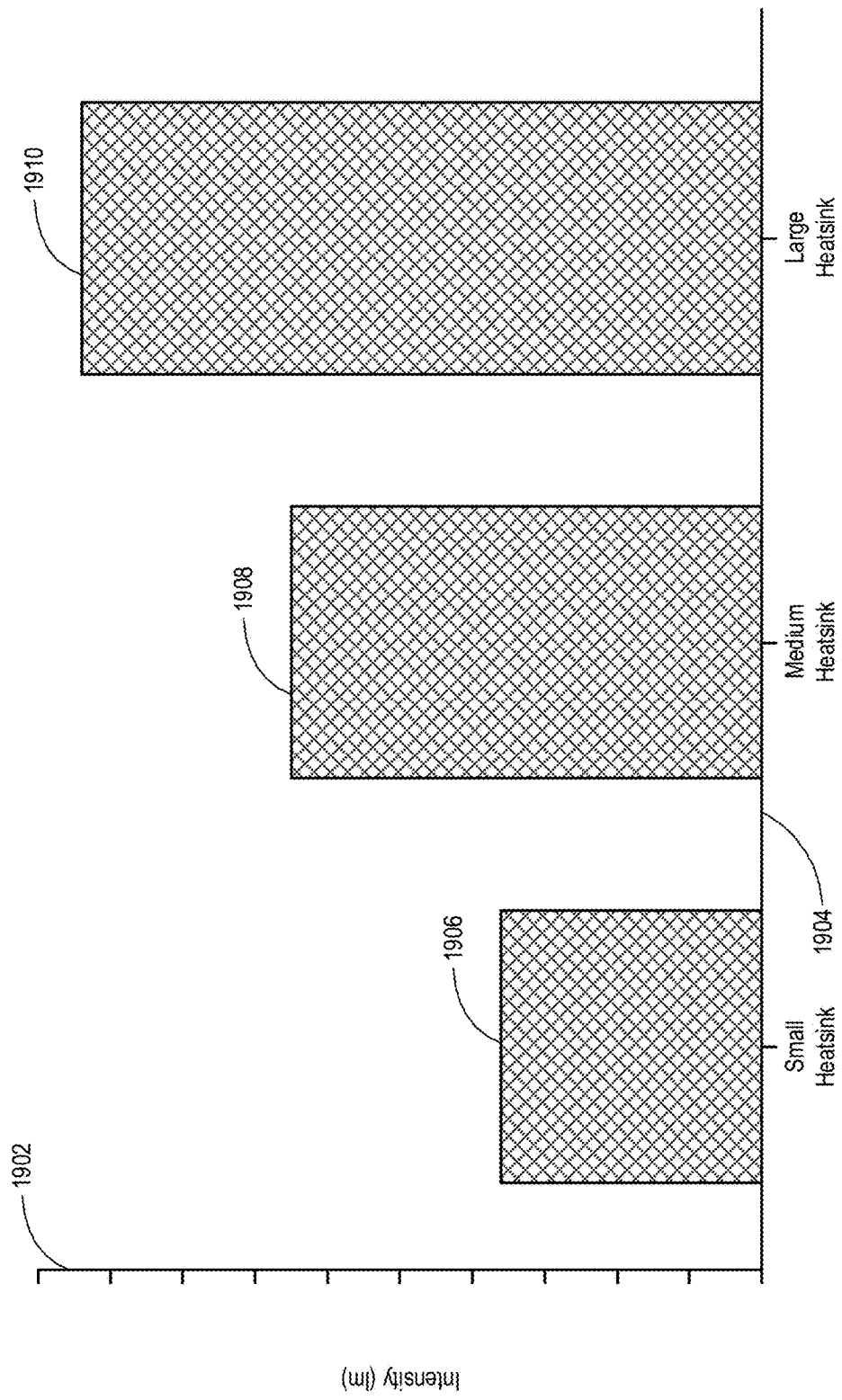
FIG. 19 illustrates the intensity of the LED lighting system with different sizes of heat sinks attached.

FIG. 19 illustrates an intensity 1902 of the LED lighting system with different sizes of heat sinks 1904 attached. The LED lighting system may vary the intensity 1902 to limit the temperature of the LEDs. Because each heat sink is capable of dissipating heat at a different rate, the LED lighting system may increase the intensity 1902 with a more capable heat sink. For example, as shown, the intensity 1902 when a small heat sink is attached 1906 is less than the intensity 1902 when a medium heat sink is attached 1908, and similarly, the intensity 1902 when a medium heat sink is attached 1908 is less than when a large heat sink is attached 1910.

The various embodiments of systems and methods described herein improve the flexibility of LED lights in various industry and residential applications. The above description provides numerous specific details for a thorough understanding of the embodiments described herein; however, one or more of the specific details may be omitted, modified, and/or replaced by a similar process or system.

What is claimed:

1. An LED lighting system, comprising:
   a plurality of light-emitting diodes (LEDs);
   at least one driver to drive the plurality of LEDs at a drive frequency; and
   a programmable signal generator to control the drive frequency, comprising:
      a clock,
      an input module to receive commands to modify the drive frequency of one or more of the plurality of LEDs to a target frequency during a time period, and
      a frequency adjustment module to modify the drive frequency of the one or more of the plurality of LEDs to the target frequency during the time period.

2. The system of claim 1, wherein the drive frequency has a range of about 1 kilohertz to about 20 kilohertz.

3. The system of claim 1, wherein the input module comprises a storage device having stored thereon a plurality of target frequencies associated with a plurality of time periods.

4. The system of claim 1, wherein the input module is configured to receive use commands that specify a purpose of the plurality of LEDs, and the input module is configured to create the target frequency during the time period based on the received use commands.

5. The system of claim 1, further comprising a reporting module configured to communicate an estimated remaining life of the plurality of LEDs via a wireless communication interface.

6. An LED lighting system, comprising:
   a plurality of light-emitting diodes (LEDs);
   at least one driver to drive the plurality of LEDs at a drive frequency; and
   a programmable signal generator to control the drive frequency, comprising:
      a clock;
      an input module to receive commands specifying:
         (i) a nonzero first target drive frequency of the plurality of LEDs during a first time period, and
         (ii) a nonzero second target drive frequency of the plurality of LEDs during a second time period;
      a frequency adjustment module to modify the drive frequency of the plurality of LEDs to the first target frequency during the first time period and the second target frequency during the second time period.

7. The system of claim 6, wherein the drive frequency has a range of about 1 kilohertz to about 20 kilohertz.

8. The system of claim 6, wherein the first target drive frequency is between 1 kilohertz and 10 kilohertz, and the second target drive frequency is between 10 kilohertz and 20 kilohertz.

9. The system of claim 6, wherein the first target drive frequency is between 60 hertz and 1 kilohertz, and the second target drive frequency is between 10 kilohertz and 20 kilohertz.

10. The system of claim 6, wherein the input module comprises a storage device having stored thereon a plurality of target frequencies associated with a plurality of time periods.

11. The system of claim 6, wherein the input module is configured to receive use commands that specify a purpose of the plurality of LEDs during each of a plurality of time periods, and the input module is configured to generate a target frequency during each of the plurality of time periods based on the received use commands.

12. The system of claim 6, further comprising a reporting module configured to communicate an estimated remaining life of the LEDs via a wireless communication interface.

13. An LED lighting system, comprising:
   a light-emitting diode (LED);
   a driver to drive the LED at a drive frequency; and
   a programmable signal generator to control the drive frequency, comprising:
      an input module storing:
         (iii) a nonzero first target drive frequency of the LED during a first time period, and
         (iv) a nonzero second target drive frequency of the LED during a second time period;
      a frequency adjustment module to modify the drive frequency of the LED to the first target frequency during the first time period and the second target frequency during the second time period.

14. The system of claim 13, wherein the drive frequency has a range of approximately 1 kilohertz to about 20 kilohertz.

15. The system of claim 13, wherein the first target drive frequency is between 1 kilohertz and 10 kilohertz, and the second target drive frequency is between 10 kilohertz and 20 kilohertz.

16. The system of claim 13, wherein the first target drive frequency is less than 1 kilohertz, and the second target drive frequency is between 10 kilohertz and 20 kilohertz.

17. The system of claim 13, wherein the input module comprises a storage device having stored thereon a plurality of target frequencies associated with a plurality of time periods.

18. The system of claim 13, wherein the input module is configured to receive use commands that specify a purpose of the plurality of LEDs during each of a plurality of time periods, and the input module is configured to generate a target frequency during each of the plurality of time periods based on the received use commands.

19. The system of claim 13, further comprising a reporting module configured to communicate an estimated remaining life of the LEDs via a wireless communication interface.

* * * * *